(12) United States Patent
Cristol-Donovan

(10) Patent No.: US 10,265,889 B2
(45) Date of Patent: Apr. 23, 2019

(54) SHAPING MOLD APPARATUSES FOR MANUFACTURING A GARMENT APPARATUS

(71) Applicant: BRAZEN GOODS LLC, Los Angeles, CA (US)

(72) Inventor: Melanie Cristol-Donovan, Los Angeles, CA (US)

(*) Notice: Subject to any disclaimer, the term of this patent is extended or adjusted under 35 U.S.C. 154(b) by 138 days.

(21) Appl. No.: 15/074,992

(22) Filed: Mar. 18, 2016

(65) Prior Publication Data

US 2016/0271841 A1  Sep. 22, 2016

Related U.S. Application Data

(60) Provisional application No. 62/136,412, filed on Mar. 20, 2015, provisional application No. 62/247,754, filed on Oct. 29, 2015, provisional application No. 62/253,006, filed on Nov. 9, 2015.

(51) Int. Cl.
| | |
|---|---|
| *B29C 41/14* | (2006.01) |
| *A61F 6/04* | (2006.01) |
| *A61F 6/06* | (2006.01) |
| *A41B 9/12* | (2006.01) |
| *B29L 31/00* | (2006.01) |
| *B29L 31/48* | (2006.01) |

(52) U.S. Cl.
CPC .............. *B29C 41/14* (2013.01); *A41B 9/12* (2013.01); *A61F 6/04* (2013.01); *A61F 6/065* (2013.01); *A41B 2500/50* (2013.01); *B29L 2031/4871* (2013.01); *B29L 2031/753* (2013.01); *B29L 2031/757* (2013.01)

(58) Field of Classification Search
CPC ....... B29C 41/14; A41B 9/12; A41B 2500/50; A61F 6/065; A61F 2006/041
USPC .......................................................... 425/275
See application file for complete search history.

(56) References Cited

U.S. PATENT DOCUMENTS

| | | | | |
|---|---|---|---|---|
| 484,046 | A |   | 10/1892 | Pitman |
| 2,158,206 | A | * | 5/1939 | Spanel ............... B29D 99/0064 264/303 |
| 2,359,948 | A | * | 10/1944 | Tillotson ............ B29D 99/0064 264/224 |
| 3,079,643 | A | * | 3/1963 | Miller ...................... A41C 1/04 264/156 |
| RE26,021 | E | * | 5/1966 | Miller et al. ............. A41C 1/04 428/131 |

(Continued)

FOREIGN PATENT DOCUMENTS

| | | |
|---|---|---|
| WO | WO2001015624 A2 | 3/2001 |
| WO | WO2013020361 A1 | 2/2013 |
| WO | WO2014113764 A1 | 7/2014 |

OTHER PUBLICATIONS

International Search Report for PCT/US16/23314 dated Aug. 5, 2016.

(Continued)

*Primary Examiner* — Robert B Davis
(74) *Attorney, Agent, or Firm* — Wuersch & Gering LLP

(57) ABSTRACT

Shaping mold apparatuses and housings for manufacturing a garment apparatus are provided. The garment apparatus can be, for example, a device, a panty, a boyshort, a short, a lingerie item, a barrier, a garment, an undergarment, a membrane, a prophylactic, and/or a system.

20 Claims, 28 Drawing Sheets

(56) References Cited

U.S. PATENT DOCUMENTS

| | | |
|---|---|---|
| 3,679,342 A * | 7/1972 | Fougeray .............. B05C 19/02 425/275 |
| 3,905,372 A | 9/1975 | Denkinger |
| 4,807,611 A | 2/1989 | Johnson |
| 4,815,456 A | 3/1989 | Consentino et al. |
| 4,828,491 A | 5/1989 | Gray |
| 4,840,624 A | 6/1989 | Lee |
| 4,862,901 A | 9/1989 | Green |
| 4,949,731 A | 8/1990 | Harding |
| 4,967,767 A | 11/1990 | Harris et al. |
| 4,981,147 A | 1/1991 | Barnett |
| 4,993,433 A | 2/1991 | Reddy |
| 5,086,519 A | 2/1992 | Rokasky |
| 5,146,930 A | 9/1992 | Richardson et al. |
| 5,269,320 A | 12/1993 | Hunnicutt |
| 5,320,112 A | 6/1994 | Bloodsaw |
| 5,358,500 A | 10/1994 | Lavon et al. |
| 5,388,592 A | 2/1995 | Williams |
| 5,390,681 A | 2/1995 | Daley |
| 5,515,862 A | 5/1996 | Artsi et al. |
| 5,535,757 A | 7/1996 | Fleming |
| 5,582,187 A | 12/1996 | Hussey |
| 5,596,997 A | 1/1997 | Abadi |
| 5,687,741 A | 11/1997 | Torger |
| 5,701,608 A | 12/1997 | Kohn |
| 5,742,936 A | 4/1998 | Tronc |
| 5,769,090 A | 6/1998 | Brown |
| 5,785,052 A | 7/1998 | Johnson |
| 6,035,853 A | 3/2000 | Alla |
| 6,360,746 B1 | 3/2002 | Harrison |
| 6,527,757 B1 | 3/2003 | Jackson |
| 6,694,980 B2 | 2/2004 | Anderson |
| 6,716,206 B2 | 4/2004 | Jackson |
| 6,987,210 B1 | 1/2006 | Giloh |
| 7,137,972 B1 | 11/2006 | Holberg |
| 7,392,807 B2 | 7/2008 | Osterberg |
| 7,823,591 B2 | 11/2010 | Reddy et al. |
| 7,858,841 B2 | 12/2010 | Krautkramer et al. |
| 7,901,740 B2 | 3/2011 | Giloh |
| 7,963,285 B2 | 6/2011 | Attilla |
| 8,141,554 B2 | 3/2012 | Olivera |
| 2005/0115568 A1 | 6/2005 | Martin |
| 2006/0042639 A1 | 3/2006 | Wallace |
| 2008/0302367 A1 | 12/2008 | Walker et al. |
| 2013/0056008 A1 | 3/2013 | Bone et al. |
| 2013/0133665 A1 | 5/2013 | Waller |
| 2013/0298913 A1 | 11/2013 | Dixon et al. |
| 2014/0202468 A1 | 7/2014 | Parsi |
| 2014/0317821 A1 | 10/2014 | Berns |

OTHER PUBLICATIONS

Written Opinion for PCT/US16/23314 dated Aug. 5, 2016.
http://glydehealth.com/products/sheer-glyde-dams/.
http://www.syren.com/c-189-latex-stockings-lingerie.aspx.

* cited by examiner

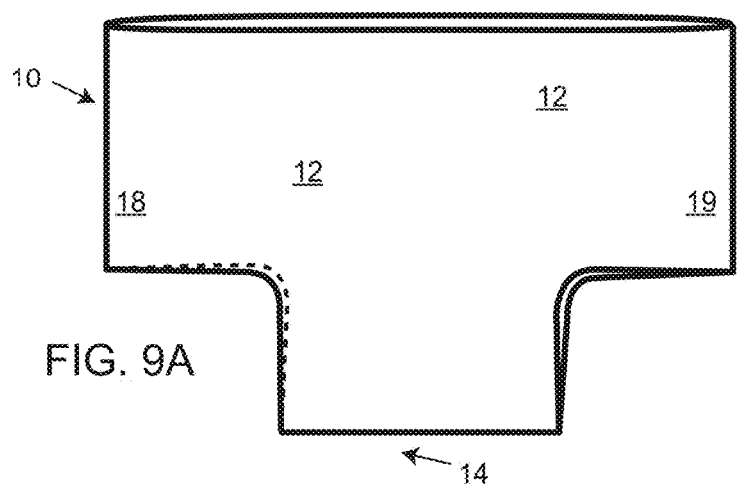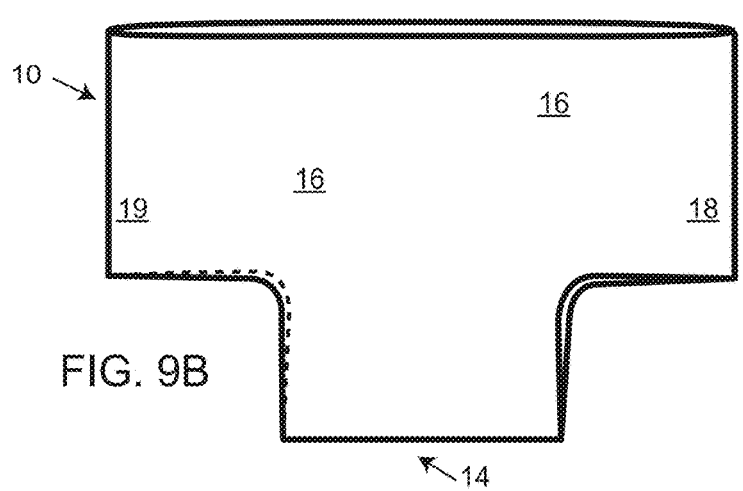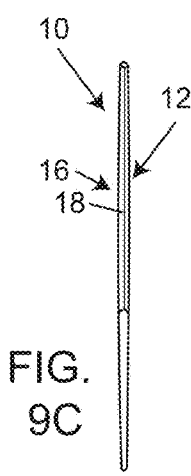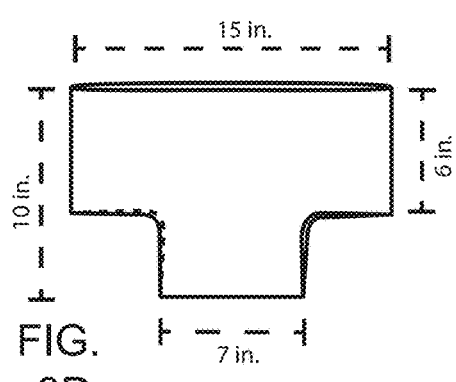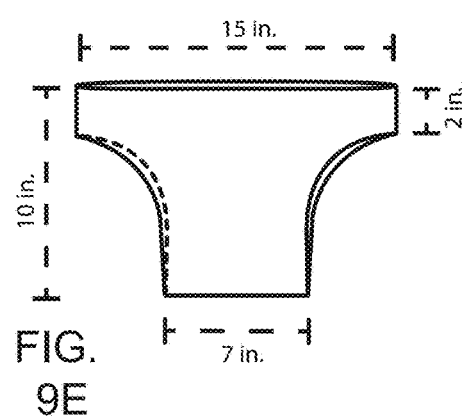

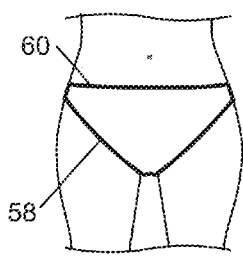
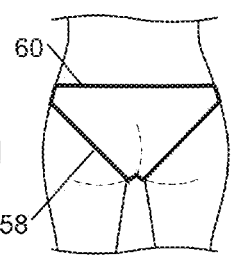
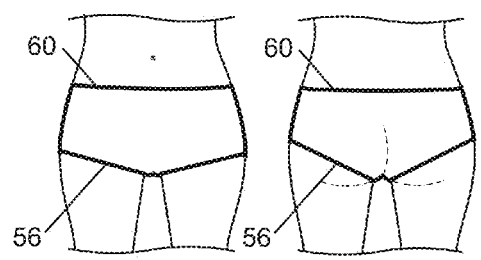
FIG. 11A  FIG. 11B
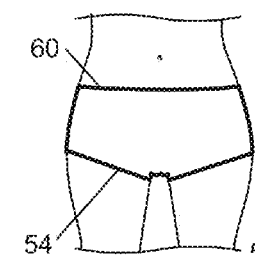
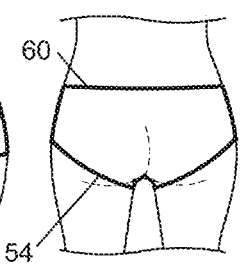
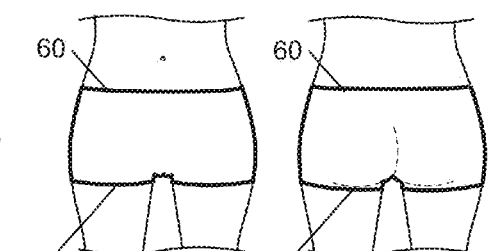
FIG. 11C  FIG. 11D
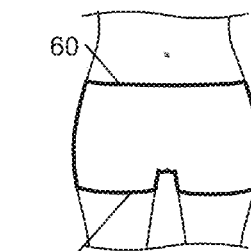
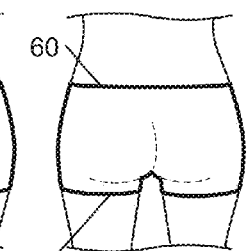
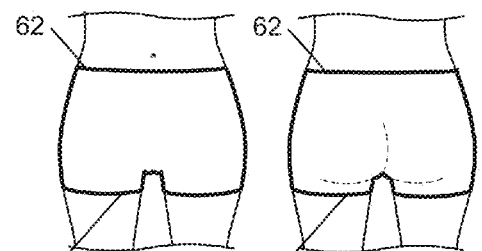
FIG. 11E  FIG. 11F
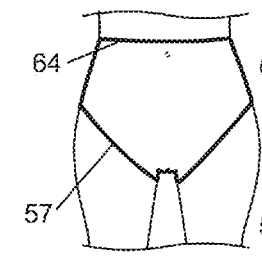
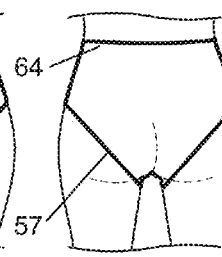
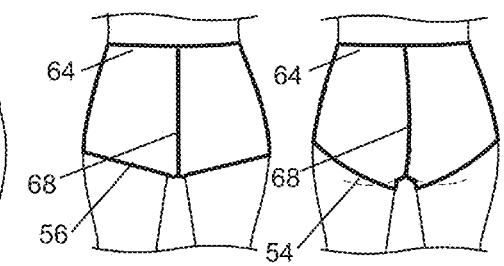
FIG. 11G  FIG. 11H

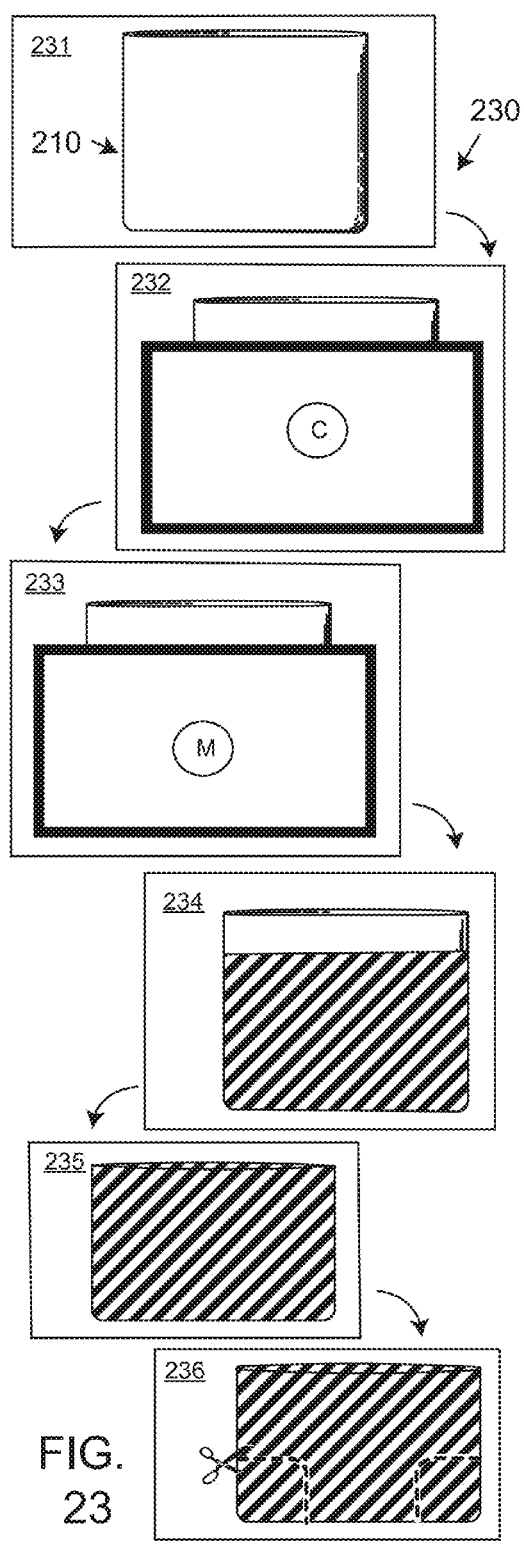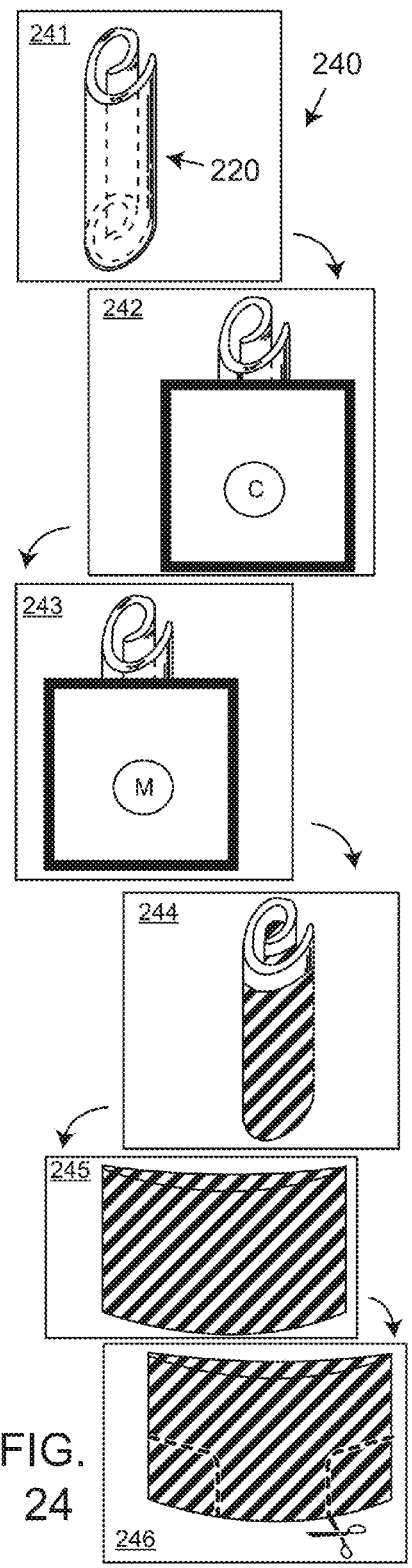
FIG. 23
FIG. 24

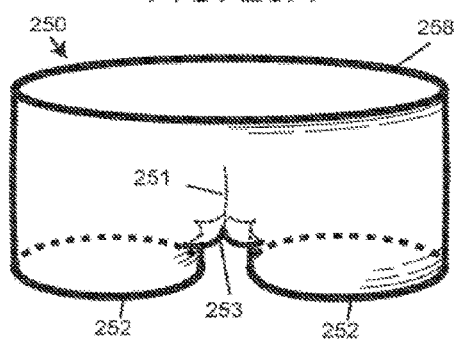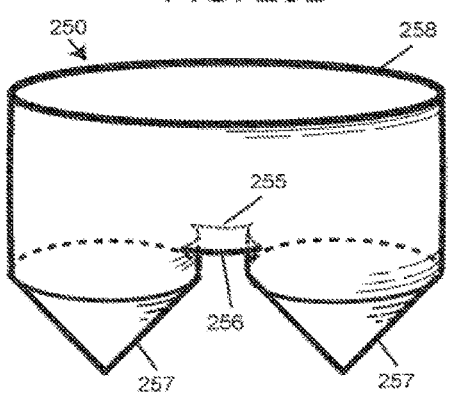

SHAPING MOLD APPARATUSES FOR MANUFACTURING A GARMENT APPARATUS

CROSS-REFERENCE TO RELATED APPLICATIONS

The present invention claims priority to: U.S. Provisional Patent Application Ser. No. 62/136,412, having title "Barrier Undergarment for Oral Sex," filed on Mar. 20, 2015; U.S. Provisional Patent Application Ser. No. 62/247,754, having title "Barrier Garment," filed on Oct. 29, 2015; and U.S. Provisional Patent Application Ser. No. 62/253,006, having title "Barrier Garment," filed on Nov. 9, 2015, each of these three patent applications being hereby incorporated by reference in its entirety. Cross-reference is made to U.S. patent application Ser. No. 15/075,000, having title "Methods of Manufacturing a Garment Apparatus," filed on Mar. 18, 2016, the entirety of which is hereby incorporated by reference in its entirety. Cross-reference is made to U.S. patent application Ser. No. 15/074,968, having title "Barrier Garment," filed on Mar. 18, 2016, the entirety of which is hereby incorporated by reference in its entirety.

FIELD OF THE INVENTION

The present invention relates to a system, method, method for manufacturing, and apparatus, among other things, for a garment, specifically a garment to serve as a barrier. More specifically, the present invention relates to a manufactured good, a method for manufacturing the good, a mold to be used in manufacturing the good, and a method of using the good. More specifically, the present invention relates to a prophylactic or barrier for sexual activity, including prophylactics and barriers for performing oral sex on the vulva, perineum, and/or anus.

RELATED INFORMATION

Prophylactics for sexual activity have been made available for years. These prophylactics, however, address limited modes of sexual activity and do not necessarily allow for additional modes of sexual activity. For example, cunnilingus, while once stigmatized, is now commonplace in people's sex lives, and oral-anal sex has increased in popularity over the past few years. But, not everyone who enjoys oral sex can receive it as frequently as they might wish.

For example, couples might engage in a less-than-optimal amount of oral sex due to one or both partners' known sexually transmitted infection(s) (STIs) or fear of an unknown infection. Diseases such as herpes, human papillomavirus (HPV), human immunodeficiency virus (HIV), hepatitis, chlamydia, syphilis, and gonorrhea can each be spread through one or more components of oral sex: fluid transfer, contact of one person's skin with another's ulcerations, and even contact of one person's skin with another's un-ulcerated skin. The areas with risk of spreading a disease include not only the vulva, perineum, and anus, but also the lower abdomen, the upper thighs, and the buttocks. A person can transmit a disease without knowledge and/or physical evidence that the person is infected. The Centers for Disease Control estimate that men and women in the United States have a total of 110 million STIs. Researchers also estimate that, in the United States, one out of every five adults has genital herpes, and one out of every four adults has HPV. Further, it is estimated that one out of every two sexually active Americans will contract an STI by age 25.

In addition to STIs, couples might engage in a less-than-optimal amount of oral sex due to the oral-sex performer's personal preference regarding the taste and scent of the oral-sex receiver's vaginal, perineal, or anal area; due to the receiver's feelings about their own taste or scent; or because the receiver is menstruating.

Many of these concerns could be fully or partially ameliorated through the use of a prophylactic or another barrier; and, in a better scenario, oral sex would be equally pleasurable—if not more pleasurable—while using such a barrier. Available techniques tend to decrease oral-sex participants' pleasure in one or more of the following ways. For example, an apparatus must be held in place while in use. This can prevent the full use of the performer's and recipient's hands for additional sexual stimulation or other activity. For example, an apparatus—while designed to be hands-free—is insufficiently stable, and moves around on the body during the act of oral sex or other physical activity. This slippage can allow for transfer of anal bacteria to the vagina, leading to urinary tract infections. In addition, this slippage can allow for the very consequences described above that prophylactics are intended to prevent, i.e., fluid transfer and skin-to-skin contact. For example, an apparatus, even if it were to stay properly in place, does not cover enough surface area of the body to prevent transmission of certain diseases. For example, an apparatus is too thick and/or stiff for a recipient to feel movements of the performer, leading to less pleasure for the recipient and additional fatigue for the performer. For example, an apparatus has too much excess material, thus diminishing sensation for the recipient and causing difficulty in breathing or even gagging or choking for the performer. For example, an apparatus is physically unattractive and detracts from the aesthetics of sexual activity. This, in turn, decreases the apparatus's utility because if it is too unappealing for people to be willing to use it, then either couples will choose to not engage in cunnilingus or disease will continue to spread. For example, an apparatus includes multiple parts making it costly to manufacture, and thus, too expensive for a typical consumer. The prohibitive cost lessens the likelihood that the product will be used as needed and can create undue pressure on the couple to make each sexual encounter worthwhile to justify the cost.

These drawbacks of available apparatuses, especially when in combination, make it more difficult for couples to enjoy oral sex. Female recipients are particularly susceptible to these drawbacks due to, according to documented research, women being more easily distracted during sex and less likely to achieve climax than men.

In practice, the two apparatuses most commonly used for protection during cunnilingus were developed for entirely different, non-sexual purposes. These two apparatuses suffer from several of the drawbacks described above.

First, some couples use sheets of latex known as dental dams, which were originally developed for use in dentistry, for protection during oral sex. Dental dams (also known as "oral dams" or merely "dams") suffer from many of the problems listed above. For example, the dam must be held in place during sexual activity, requiring concentration and agility, thus detracting from the participants' focus and enjoyment. For example, if the recipient moves during sexual activity, it becomes very difficult to hold the dam in place. If the dam undesirably moves even a few inches, bacteria can be transmitted from the anus to the vagina, among other unwanted events. Or, for example, if the dam moves while the performer is engaging in oral sex, the performer's mouth can touch the recipient's skin, allowing potential disease to be spread. Further, for example, the material of the dam can gather in the performer's mouth during sexual activity and lead to difficulty breathing, gagging, and/or choking. And, even when the dam is properly held in place, the dam is not large enough to simultaneously cover portions of the thighs, lower abdomen, and buttocks, which can carry and transmit diseases such as HPV and herpes. Further, for example, such dams may be untasteful and/or emit undesired odors due to material and/or due to the loose fit on the wearer. While oral sex on both males and females appears to be increasing, according to various studies, condoms on males appear to be used much more frequently than dental dams on females. Possible conclusions drawn from this include that dental dams do not satisfy the apparent market need and are not perceived to be as easy or as desirable to employ as the male prophylactic counterpart.

Second, some couples use ordinary plastic wrap, which was originally developed for wrapping and sealing food items, for protection during oral sex. Certain varieties of plastic wrap are known to be porous and can allow for the transmission of viruses, bacteria, scent, and taste. Further, plastic wrap suffers from many of the problems listed above when held against a recipient's body for oral sex. For example, the plastic wrap during sexual activity becomes very wrinkled, making it difficult for the performer to navigate the vulva, clitoris, anus, and perineum, i.e., the "genital region". For example, the plastic wrap during sexual activity can get sucked into the nostrils of the performer, causing difficulty breathing and/or a suffocating feeling. For example, the plastic wrap can gather in the performer's mouth and lead to gagging. Further, for example, similar to the dental dam, the plastic wrap must be held in place during use. The plastic wrap can easily slip out of place—particularly when the recipient moves their body—allowing the spread of disease and bacteria, among other things.

In an effort to allow hands-free use of dental dams and plastic wrap, straps have been attached to the dental dams and/or plastic wrap. See, for example, U.S. Pat. No. 5,388,592 to Williams (1995) and U.S. Pat. No. 4,862,901 to Green (1989). In theory, the attached straps are used in order to allow the hands to be free during sexual activity. However, in practice, the thin material of the straps provides insufficient support, and the dam moves around the genital region when the performer provides pressure and/or vigorous movement. Due to the dam moving, it is difficult to prevent contact between the performer's mouth and the receiver's body, and inter alia, for example, prevent bacteria transfer from the anus to the vagina. Such apparatuses cover an insufficient amount of surface area to protect against skin-to-skin contact with areas such as the inner and upper thighs and the lower buttocks. Such apparatuses often include multiple components causing them to be expensive to manufacture and for the consumer to purchase. Such apparatuses in their complexity also cause a consumer additional time in figuring out how to properly utilize the apparatuses and take additional time to put on, decreasing the enjoyment and spontaneity of sexual activity.

Other available apparatuses include novelty rubber underwear that some suggest be used as a barrier during cunnilingus. Novelty rubber underwear is meant as a fashion item for people with a latex fetish. It is not a feasible barrier because, for example, oral sex cannot be comfortably or safely performed using novelty rubber underwear and similar novelty products. Further, these types of novelty products are not usually made for oral use, and, accordingly, latex and other materials allergies can be an impediment. For example, at 0.33 to 0.50 millimeters in thickness, these novelty garments are several times thicker than typical dental dams. The novelty garments are so thick that only a minimal amount of pressure or sensation can be transferred from the performer's mouth and tongue to the recipient's genital region, leading to less pleasure for the recipient. Further, the thickness of the novelty garments requires the performer to exert more energy and pressure performing oral sex, leading to fatigue. Further, the novelty garments do not have nearly enough pliability for a tongue to penetrate a vagina or anus. Further, the thickness of these novelty garments causes them to be difficult and time-consuming to put on, making the novelty garments unsuitable for spontaneous sexual activity. Further, these novelty garments cannot be used safely as a prophylactic because they are not quality-checked for porousness and they do not provide adequate coverage of portions of the body (such as the inner and upper thighs and the lower buttocks) that can contain STIs.

Accordingly, there is a need in the industry for a hands-free apparatus to use during oral sex on a vulva, perineum, and anus that is both aesthetically attractive and stays in place. There is also a need in the industry for such an apparatus that provides adequate coverage and prevents skin-to-skin contact with bodily areas other than and including the genital region, i.e., the vulva, perineum, and anus. There is also a need for a hands-free apparatus to use during oral sex that fits a variety of different body shapes, while still providing adequate coverage. Further, there is a need in the industry for a hands-free apparatus that is directed towards allowing a variety of pleasurable interactions, and not directed solely towards penetration.

SUMMARY

The present invention is a barrier—as well as a shaping mold, a method of use, and a method of manufacture for said barrier—shaped like an undergarment that is worn during oral-vaginal and oral-anal sex to protect another person's mouth, lips, tongue, saliva, nose, and breath from contact with the wearer's vulva, perineum, anus, and surrounding areas, in order to prevent the transmission of bacteria, sexually transmitted infections, taste, and scent. The barrier is thin, substantially non-porous, elastic, skin-tight, and aesthetically attractive. The barrier can be, for example, a device, a panty, a boyshort, a short, a lingerie item, a garment, an undergarment, a membrane, an apparatus, and/or a system.

Advantages of one or more aspects of embodiments of the present invention are as follows: to provide a barrier for oral sex on a vulva, perineum, and/or anus that need not be held in place during sexual activity, that is sufficiently stable and relatively immobile during sexual activity, that is not loose or movable enough to allow anal bacteria to be easily transferred to the vagina during sex, that covers up enough surface area of the body to prevent transmission of a variety of diseases, that is fluid impermeable, that is virus impermeable, that is pliable enough to allow full penetration by a tongue but not so pliable as to create excess material, that is pliable enough to stretch to fit bodies of multiple sizes, that includes only a single thin layer of material between the oral cavity of the performer and the genital area of the wearer, that is substantially skin tight and curves around crevices while at rest, that causes few aesthetic and/or operational distractions for the participants, that includes few parts, that allows for disposability for cost and/or environment reasons and/or ease of use, and that is inexpensive for a manufacturer to produce and for a consumer to purchase. Other advantages of one or more aspects will be apparent from a consideration of the drawings and ensuing description.

Further, embodiments of the present invention can be used in the film industry, at sporting events, and in other arenas. For example, an embodiment of the present invention provides for a translucent, thin garment which allows a specific flexibility, movement, and/or sensation.

An embodiment of the present invention provides for a garment having: a membrane formed of elastomeric material, the membrane including: a front portion, a back portion, an outer thigh portion on a right side of the membrane, an outer thigh portion on a left side of the membrane, and a genital portion; wherein the front portion and the back portion of the membrane are joined via the outer thigh portion on the respective right and left sides of the membrane so as to form an opening at a top portion of the membrane; and wherein the front portion and the back portion of the membrane are joined via the genital portion, and each outer thigh portion of the respective right and left sides of the membrane are joined via the genital portion to form a respective opening on each of the right and left sides of the membrane.

An embodiment of the present invention provides for a garment having: a membrane formed of elastomeric material, the membrane including: a front portion, a back portion, an inner thigh portion and an outer thigh portion on a right side of the membrane, an inner thigh portion and an outer thigh portion on a left side of the membrane, and a genital portion; wherein the front portion and the back portion of the membrane are joined via the outer thigh portion on the right and left sides of the membrane so as to form an opening at a top portion of the membrane; and wherein the front portion and the back portion of the membrane are joined via the genital portion and the inner thigh portions, respectively, on the right and left sides of the membrane, the front and back portions and the inner thigh portions of the right and left sides of the membrane all joining the genital portion of the membrane, and the inner and outer thigh portions, respectively, on the right and left sides of the membrane form an opening on each of the right and left sides of the membrane.

An embodiment of the present invention provides for a garment having: a membrane formed of elastomeric material which is at least one of: a completely non-permeable material, a partially non-permeable material, a partially pliable material, and a completely pliable material, the membrane including: a front portion, a back portion, an outer thigh portion on a right side of the membrane, an outer thigh portion on a left side of the membrane, and a genital portion; wherein the front portion and the back portion of the membrane are joined via the outer thigh portion on the respective right and left sides of the membrane so as to form an opening at a top portion of the membrane; and wherein the front portion and the back portion of the membrane are joined via the genital portion, and each outer thigh portion of the respective right and left sides of the membrane are joined via the genital portion to form a respective opening on each of the right and left sides of the membrane; and wherein the membrane includes at least one seam in the genital portion so as to maximize a skin-tight fit effect of the membrane.

An embodiment of the present invention provides for a garment having: a membrane formed of elastomeric material which is at least one of: a completely non-permeable material, a partially non-permeable material, a partially pliable material, and a completely pliable material, the membrane including: a front portion, a back portion, two thigh portions, and a genital portion; wherein the front portion and the back portion of the membrane are joined so as to form an opening at a top portion of the membrane; wherein the front portion and the back portion of the membrane are joined so as to form the genital portion for covering a human genital region and to form the two thigh portions for covering at least part of two respective thigh regions; wherein the membrane includes at least one crease in the genital portion so as to maximize a skin-tight fit effect of the membrane.

In an embodiment of the present invention, the membrane is seamless. In an embodiment of the present invention, the front portion and the back portion of the membrane are interchangeable. In an embodiment of the present invention, the membrane is at least one of: a completely non-permeable material, a partially non-permeable material, a partially pliable material, and a completely pliable material. In an embodiment of the present invention, the partially non-permeable material has at least one of: a microscopic opening, a deficiency in the material, a weakness in the material, and an opening for design purposes. In an embodiment of the present invention, the partially pliable material is at least one of: material having a non-flexible region and material having a reduced flexibility region.

In an embodiment of the present invention, the top portion of the membrane fits a torso snugly. In an embodiment of the present invention, the membrane fits a thigh region snugly. In an embodiment of the present invention, the entire membrane fits a wearer's body snugly. In an embodiment of the present invention, the outer thigh portions on the right and left sides of the membrane fit a human wearer's respective thigh areas snugly. In an embodiment of the present invention, the two thigh portions of the membrane fit the respective thigh regions snugly. In an embodiment of the present invention, the membrane is made as one size fits all. In an embodiment of the present invention, the membrane is made in different sizes from molds of different sizes to account for different wearers' different sizes.

In an embodiment of the present invention, the membrane thickness is at least one of: 0.33 millimeters, less than 0.33 millimeters, and greater than 0.33 millimeters. In an embodiment of the present invention, the two outer thigh portions each have a height of at least one of: at least 10 millimeters, at least 1 inch, at least 2 inches, at least 3 inches, at least 4 inches, at least 5 inches, at least 6 inches, at least 8 millimeters, at least 0.8 inches, at least 1.8 inches, at least 2.8 inches, at least 3.8 inches, at least 4.8 inches, at least 5.8 inches, and at least a length which extends from at least 8 millimeters below a user's genital region to a top of a pelvic bone of the user. In an embodiment of the present invention, at least one of a respective outer thigh portion of the right side and the left side and a respective outer edge of a right side and a left side of the genital portion adjacent to the respective outer thigh portion each have a height of at least one of: at least 1 millimeter, at least 8 millimeters, at least 0.8 inches, at least 1.8 inches, at least 2.8 inches, at least 3.8 inches, at least 4.8 inches, at least 5.8 inches, and at least a length measuring from 8 millimeters below a human user's genital region to a top of a pelvic bone of the human user. In an embodiment of the present invention, the membrane is one of disposable and reusable. In an embodiment of the present invention, the membrane embodies at least one of: a thong shape, a bikini shape, a legging shape, a capri pant shape, high thigh cut shape, a low-rise cut shape, a tanga shape, a cheeky shape, a boy short shape, and a boxer brief shape. In an embodiment of the present invention, the genital portion of the membrane—that is, the area extending from thigh to thigh covering what would be a human wearer's genital region—has a width greater than the human genital region. In an embodiment of the present invention, the genital portion of the membrane has a width that extends past each of a respective inner thigh portion of a right and a left side, being adjacent to the respective outer thigh portion of the right and the left sides, so that an excess membrane material is gathered next to at least one of the respective inner thigh portion of the right and the left side. In an embodiment of the present invention, the genital portion has a width such that the right side and left side provide an excess membrane material, such that when worn the excess membrane material gathers at at least one of the inner thigh portion of the right side and the inner thigh portion of the left side. In an embodiment of the present invention, a first portion of the membrane is adjacent to the top opening, and a second and a third portion of the membrane is adjacent to the respective opening formed by the respective outer thigh portions and the genital portion, the first, second and third portions being a part of the membrane and having a thickness greater than a remaining part of the membrane. In an embodiment of the present invention, a first portion of the membrane is adjacent to the top opening, the first portion being a part of the membrane, the first portion of the membrane having a smaller circumference than a remaining part of the membrane. In an embodiment of the present invention, a second portion of the membrane is adjacent to the opening on the right side and wherein a third portion of the membrane is adjacent to the opening on the left side, the second and third portions each having a smaller circumference than the remaining part of the membrane.

In an embodiment of the present invention, the membrane includes material of at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of these materials. In an embodiment of the present invention, the membrane includes at least two layers of material. In an embodiment of the present invention, the membrane includes at least one of: a design, a color, and a pattern. In an embodiment of the present invention, the membrane includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives. In an embodiment of the present invention, the membrane includes a residing substance of at least one of: a lubricant, a powder, a flavoring, and a scent, on at least a part of the membrane. In an embodiment of the present invention, the membrane includes at least one: texture beads in the genital portion, accordion fold in the genital portion, small protuberance in the genital portion. In an embodiment of the present invention, the garment is manufactured using dip-molding. In an embodiment of the present invention, the garment is a liquid-impermeable and body-odor-reducing membrane formed in the shape of an undergarment comprised of elastomeric material. In an embodiment of the present invention, the membrane closely fits a human wearer's body, using friction between the membrane and the wearer's body to assist in keeping the membrane in place on the wearer's body during inactivity and activity. In an embodiment of the present invention, a surface area of the membrane provides for frictional contact on a user so that the membrane remains in a fixed position during use.

An embodiment of the present invention provides a process for using a garment including: inserting each of a wearer's legs through the opening at the top portion of the membrane; inserting one each of the wearer's legs through one of the respective two thigh portions; pulling the membrane so that the front portion and back portion cover the human torso and the genital portion covers the human genital region; and stretching the two thigh portions according to their lengths along the wearer's legs. An embodiment of the present invention provides a process for using a garment including: inserting each of a wearer's legs through the opening at the top portion of the membrane; inserting one each of the wearer's legs through one of the respective two thigh portions; pulling the membrane so that the front portion and back portion cover the human torso and the genital portion covers the human genital region; stretching the two thigh portions according to their lengths along the wearer's legs; and contacting an exterior portion of the genital portion of the membrane with a protuberance. An embodiment of the present invention provides a process for using a garment including: inserting each of a wearer's legs through the opening at the top portion of the membrane; inserting one each of the wearer's legs through one of the respective two thigh portions; pulling the membrane so that the front portion and back portion cover the human torso and the genital portion covers the human genital region; stretching the two thigh portions according to their lengths along the wearer's legs; and contacting an exterior portion of the genital portion of the membrane with a protuberance, wherein the protuberance is at least one of: a tongue, mouth, nose, and finger.

The various embodiments described above, as well as those described below, can be used with and without each other, in various combinations, for the present invention.

An embodiment of the present invention provides for a method of manufacturing a garment including: providing a shaping mold; contacting the shaping mold with at least one solution simultaneously or one after the other; removing the shaping mold from the at least one solution when at least one of a gelled and a solidified coating of a desired thickness is produced on the shaping mold; drying the coating on the shaping mold; separating the coating from the shaping mold; and excising any excess material from at least one of a thigh portion and a torso portion of the coating. In an embodiment, the excising of the excess material is to form the membrane into a specific garment type such as a boy short, a bikini, a panty, or other desired shape, et al.

An embodiment of the present invention provides a method of manufacturing a garment, including: providing a shaping mold; contacting the shaping mold with a solution, the solution being at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of the foregoing materials; removing the shaping mold from the solution when at least one of: a gelled and a solidified coating of a desired thickness, is produced on the shaping mold; drying the coating on the shaping mold; separating the coating from the shaping mold; and excising any excess material from at least one of a thigh portion and a torso portion of the coating. In an embodiment of the present invention, the solution includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives.

An embodiment of the present invention provides for a method of manufacturing a garment including: providing a shaping mold; contacting the shaping mold with a first solution, wherein the first solution when in contact with a second solution, causes the second solution to solidify; contacting the first solution covered shaping mold with the second solution, the second solution being at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of the foregoing materials; removing the shaping mold from the second solution when at least one of a gelled and a solidified coating of a desired thickness is produced on the shaping mold; drying the coating on the shaping mold; separating the coating from the shaping mold; and excising any excess material from at least one of a thigh portion and a torso portion of the coating. In an embodiment of the present invention, the second solution includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives.

An embodiment of the present invention provides for a method of manufacturing a garment, including: providing a shaping mold; contacting the shaping mold with a first solution, wherein the first solution when in contact with a second solution, causes the second solution to solidify; contacting the first solution covered shaping mold with the second solution, the second solution being at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of the foregoing materials; removing the shaping mold from the second solution when at least one of a gelled and a solidified coating of a desired thickness is produced on the shaping mold; drying the coating on the shaping mold; contacting the second solution covered shaping mold with at least one third solution; drying the at least one third solution coating on the shaping mold; separating the coating from the shaping mold; and excising any excess material from at least one of a thigh portion and a torso portion of the coating. In an embodiment of the present invention, the second solution includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives.

In an embodiment of the present invention, the shaping mold is in the shape of a rectangle, dual cones extending from a rectangular portion, and a planar curved portion. In an embodiment of the present invention, the shaping mold is one of: rectangular-shaped; cylindrical-shaped; curved planar shaped; planar shaped; flat planar shaped; shaped such that said front and back portions are two parallel flat planes connected via at least two edges; shaped such that said front and back portions are two parallel curved planes connected via at least two edges; and rectangular-shaped and curved into a spiral shape. In an embodiment of the present invention, the first solution is a coagulant. In an embodiment of the present invention, the coating is at least one of: a completely non-permeable material, a partially non-permeable material, a partially pliable material, and a completely pliable material. In an embodiment of the present invention, the partially non-permeable material has at least one of a microscopic opening, a deficiency in the material, a weakness in the material, and an opening for design purposes, and the partially pliable material is at least one of material having a non-flexible region and material having a reduced flexibility region. In an embodiment of the present invention, the coating is an elastomeric material having a thickness of one of: 0.33 millimeters, greater than 0.33 millimeters, and less than 0.33 millimeters. In an embodiment of the present invention, the excising of the excess material occurs so that there is a front portion and a back portion of the coating joined so as to form an opening at a top portion of the coating, and so that two thigh portions for covering at least part of two respective thigh regions are provided.

An embodiment of the present invention provides a method of manufacturing a garment, including: providing a shaping housing; contacting the shaping housing with a solution; removing the shaping housing from the solution when at least one of: a gelled and a solidified coating of a desired thickness is produced on the shaping housing; drying the coating on the shaping housing; separating the coating from the shaping housing; and excising any excess material from at least one of a thigh portion and a torso portion of the coating. In an embodiment, the solution is at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of the foregoing materials. In an embodiment of the present invention, the solution includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives. In an embodiment, the coating is at least one of: seamless and wearable by a human. In an embodiment, the coating is at least one of a completely non-permeable material, a partially non-permeable material, a partially pliable material, and a completely pliable material. In an embodiment, the partially non-permeable material has at least one of: a microscopic opening, a deficiency in the material, a weakness in the material, and an opening for design purposes. In an embodiment, the partially pliable material is at least one of: material having a non-flexible region and material having a reduced flexibility region. In an embodiment, the shaping housing is put into contact with the at least one solution more than once to create the coating that has a thickness is at least one of: 0.33 millimeters, less than 0.33 millimeters, and greater than 0.33 millimeters.

An embodiment of the present invention provides a system of manufacturing a garment, including: a shaping mold, wherein the shaping mold has a front portion, a back portion, a right and a left side portions, and a bottom portion, so that the front, back, right side, left side, and bottom portions are connected to form the shaping mold as a three-dimensional structure; at least one solution, wherein the at least one solution when in contact with the shaping mold solidifies; removing the shaping mold from a second of the at least one solution when at least one of a gelled and a solidified coating of a desired thickness is produced on the shaping mold; drying the coating on the shaping mold; contacting the second solution covered shaping mold with at least one third solution; drying the at least one third solution coating on the shaping mold; separating the coating from the shaping mold; and excising any excess material from at least one of a thigh portion and a torso portion of the coating. In an embodiment, the at least one solution is a first and a second solutions, wherein the first solution is put in contact with the shaping mold, and the second solution is put in contact with the first solution on the shaping mold, wherein the first solution when in contact with the second solution causes the second solution to solidify. In an embodiment, the at least one solution is at least one of: latex, natural rubber latex, synthetic latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, vegan material, hypoallergenic material, organic material, superelastomer, other elastomer, other polymer, other copolymer, other polyolefin, and a combination of any of the foregoing materials. In an embodiment of the present invention, the at least one solution includes additives of at least one of: ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives.

An embodiment of the present invention provides for an apparatus for forming a garment embodiment according to the embodiment described herein and those that would be readily apparent variations.

An embodiment of the present invention provides for an apparatus in the form of a shaping mold. In an embodiment, the shaping mold is a planar mold or a curved planar mold. In an embodiment, the shaping mold is a planar mold or curved planar mold that is curved as a S-shaped form, an e-shaped form, a c-shaped form, a u-shaped form, or other form in order to reduce the width of the mold. This can be useful in production, or in storage of the molds. In an embodiment, the shaping mold includes a first portion resembling a rectangular mold and two conical portions attached to the first portion. In an embodiment, the shaping mold is hollow or solid. In an embodiment, the mold is usable for a dip molding process. In an embodiment, the shaping mold is of a material that functions well with the various elastomeric-type and other type materials used. In an embodiment, the shaping mold is made of more than one material, allowing for a base material to provide a strong or resilient mold along with a different material coating which reacts appropriately with the solutions encountered to form the membrane and/or to remove the membrane. In an embodiment, the shaping mold has a coating or is made entirely of the same coating which allows for the formation of the membrane and/or easy removal of the membrane. In an embodiment, certain portions of the membrane are excised or removed before removing the membrane from the shaping mold. In an embodiment, the excising of the membrane can be effected by use of a solution in discrete manner so that the solution removes only a desired portion of the membrane. In an embodiment, the excising of the membrane can be effected by the use of a knife, scissors, or other device used to cut or remove a desired portion of the membrane.

An embodiment of the present invention provides for a mold with a housing having a front portion, a back portion, a right and a left side portions, and a bottom portion, so that the front, back, right side, left side, and bottom portions are connected to form the housing as a three-dimensional structure, wherein the housing allows for being dip-molded in a solution which at least semi-solidifies on the housing. In an embodiment, the housing is one of: rectangular-shaped; cylindrical-shaped; curved planar shaped; planar shaped; flat planar shaped; shaped such that said front and back portions are two parallel flat planes connected via at least two edges; shaped such that said front and back portions are two parallel curved planes connected via at least two edges; and rectangular-shaped which is curved into a spiral shape. In an embodiment, the front and back portions are planar curved. In an embodiment, the mold is a flat planar mold in a U-shape with curved corners to allow for less waste of material and/or solution. In an embodiment, the mold is a curved planar mold in a U-shape with curved corners to allow for less waste of material and/or solution. In an embodiment, a flat planar mold has a cut-out in the middle of the bottom part of the mold simulating the legs of a boy-short version. In an embodiment, a curved planar mold has a cut-out in the middle of the bottom part of the mold simulating the legs of a boy-short version. In an embodiment, the housing is at least one of: filled with solid material, hollow, and partially filled with material. In an embodiment, the housing allows for the use of an apparatus to attach to a top portion of the housing, the apparatus being used to do at least one of: holding the housing during dip-molding, holding the housing during drying, and holding the housing during removal of material. In an embodiment, the apparatus is at least one of: a gripping device, a wire, a hanging device, a screwed-in device, a magnetic device, or other attachment or positioning or holding device. In an embodiment, the housing is made of at least two materials wherein a first of the at least two materials is a material resistant to corrosion, and a second of the at least two materials is a material which does not permanently bind with polymer solution, wherein the second of the at least two materials is layered over the first of the at least two materials. In an embodiment, the housing is composed of a material that is coatable with a completely non-permeable material, a partially non-permeable material, a partially pliable material, and a completely pliable material. In an embodiment, the housing is coatable by a coating that is an elastomeric material having a thickness of one of: 0.33 millimeters, less than 0.33 millimeters, and greater than 0.33 millimeters. In an embodiment, the housing has a material coating which allows for at least one of: a formation of a membrane from a solidifying solution, a removal of a membrane formed from a solidifying solution on the housing, and resistance to sharp cutting instruments.

An embodiment of the present invention provides for a mold on which a garment can be formed, including: a rectangular-shaped housing having a front portion, a back portion, a left side portion, and a right side portion, wherein the front portion, back portion, and left side and right side portions, are connected to each other to form a three-dimensional rectangular-shaped housing; a first cylindrical housing, wherein a top portion edge of the first cylindrical housing is connected to a bottom portion edge of the rectangular-shaped housing, so that the top portion edge of the first cylindrical housing is connected with the left side portion, the front portion, and the back portion; a second cylindrical housing, wherein a top portion edge of the second cylindrical housing is connected to the bottom portion edge of the rectangular-shaped housing, so that the top portion edge of the first cylindrical housing is connected with the right side portion, the front portion, and the back portion; and, a middle portion having a front edge, a back edge, a right side edge and a left side edge, wherein the middle portion front edge is connected to the rectangular-shaped housing front edge, the middle portion back edge is connected to the rectangular-shaped housing back edge, the middle portion right side edge is connected to the second cylindrical housing, and the middle portion left side edge is connected to the first rectangular-shaped housing. In an embodiment, the first cylindrical housing and the second cylindrical housing are each at least one of: an ellipsoid and an ovoid In an embodiment, a mold includes a first conical portion connected to a bottom portion edge of the first cylindrical housing; and a second conical portion connected to a bottom portion edge of the second cylindrical housing. In an embodiment, the housing is made of at least two materials wherein a second of the at least two materials is a material which does not bind with coagulants, wherein the second of the at least two materials is layered over a first of the at least two materials. In an embodiment, the housing is coatable with a completely non-permeable material, a partially non-permeable material, a partially pliable material, and a completely pliable material. In an embodiment, the housing has a material coating which allows for at least one of: a formation of a membrane from a solidifying solution, a removal of a membrane formed from a solidifying solution on the housing, and resistance to sharp cutting instruments. In an embodiment, the housing is at least one of: filled with solid material, hollow, and partially filled with material. In an embodiment, the housing allows for the use of an apparatus to attach to a top portion of the housing, the apparatus being used to do at least one of: holding the housing during dip-molding, holding the housing during drying, and holding the housing during removal of material. In an embodiment, the apparatus is at least one of: a gripping device, a wire, a hanging device, a screwed-in device, and a magnetic device. In an embodiment, the first and second cylindrical shaped housings are sized to fit a thigh of a human.

In an embodiment of the present invention, a mold for forming the barrier garment is solid material, not having a hollowed interior. In an embodiment of the present invention, the solid material can be chosen to allow for a transfer of heat or a non-transfer of heat. In an embodiment of the present invention, a mold for forming the barrier garment is a hollowed structured housing. In an embodiment of the present invention, a mold is a hollowed structured housing allowing for less cost of materials and process for manufacturing the mold. In an embodiment of the present invention, a mold for forming the barrier garment is planar curved, planar flat, planar S shaped, planar curved C shaped, planar curved E shaped, planar curved U shaped, or another type of planar curved shape for manufacturing, and a three dimensional rectangular-like shape.

BRIEF DESCRIPTION OF THE DRAWINGS

FIG. 9A shows a front view of an embodiment of the present invention.

FIG. 9B shows a rear view of an embodiment of the present invention.

FIG. 9C shows a left side view of an embodiment of the present invention folded such that the back portion and the front portion touch.

FIG. 9D shows a front view and measurements of an embodiment of the present invention.

FIG. 9E shows a front view and measurements of an embodiment of the present invention.

FIG. 11A shows a front and rear view of an embodiment of the present invention as worn on a body.

FIG. 11B shows a front and rear view of an embodiment of the present invention as worn on a body.

FIG. 11C shows a front and rear view of an embodiment of the present invention as worn on a body.

FIG. 11D shows a front and rear view of an embodiment of the present invention as worn on a body.

FIG. 11E shows a front and rear view of an embodiment of the present invention as worn on a body.

FIG. 11F shows a front and rear view of an embodiment of the present invention as worn on a body.

FIG. 11G shows a front and rear view of an embodiment of the present invention as worn on a body.

FIG. 11H shows a front and rear view of an embodiment of the present invention as worn on a body.

FIG. 23 shows a flowchart of a manufacturing process embodiment using a substantially planar flat mold form embodiment of the present invention.

FIG. 24 shows a flowchart of a manufacturing process embodiment using a substantially planar curved mold form embodiment of the present invention.

FIG. 25A shows a semi-anatomical mold embodiment with a flat bottom for manufacturing a garment embodiment of the present invention.

FIG. 25B shows a semi-anatomical mold embodiment with a conical bottom for manufacturing a garment embodiment of the present invention.

DETAILED DESCRIPTION

Figure 1A:
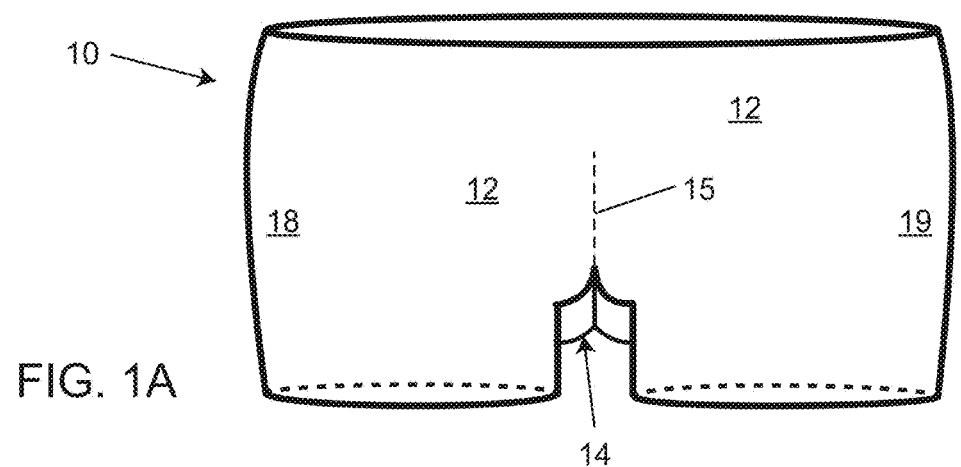
FIG. 1A shows a front view of an embodiment of the present invention.
Figure 1B:
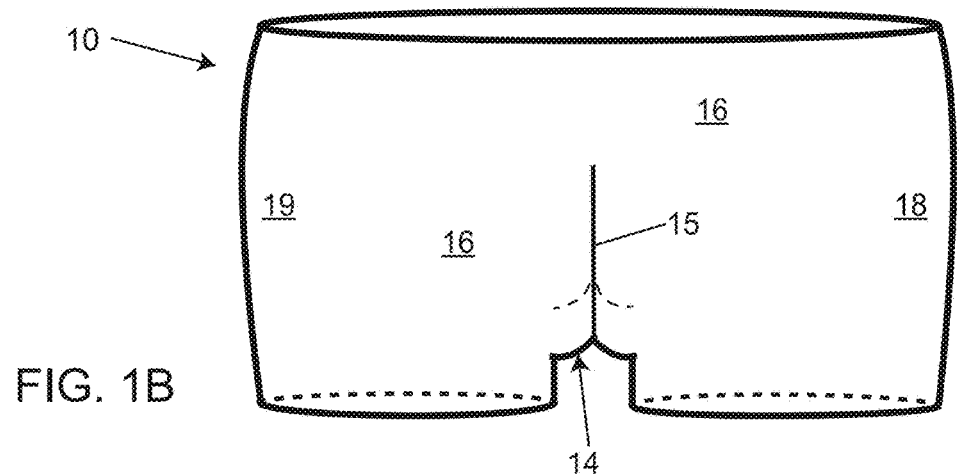
FIG. 1B shows a rear view of an embodiment of the present invention.
Figure 1C:
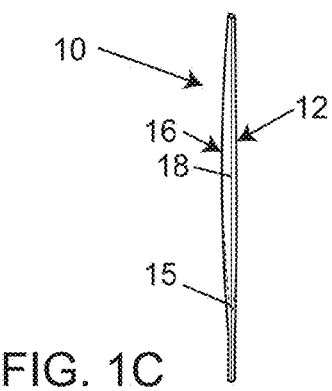
FIG. 1C shows a left side view of an embodiment of the present invention folded such that the back portion and the front portion touch.
Figure 2:
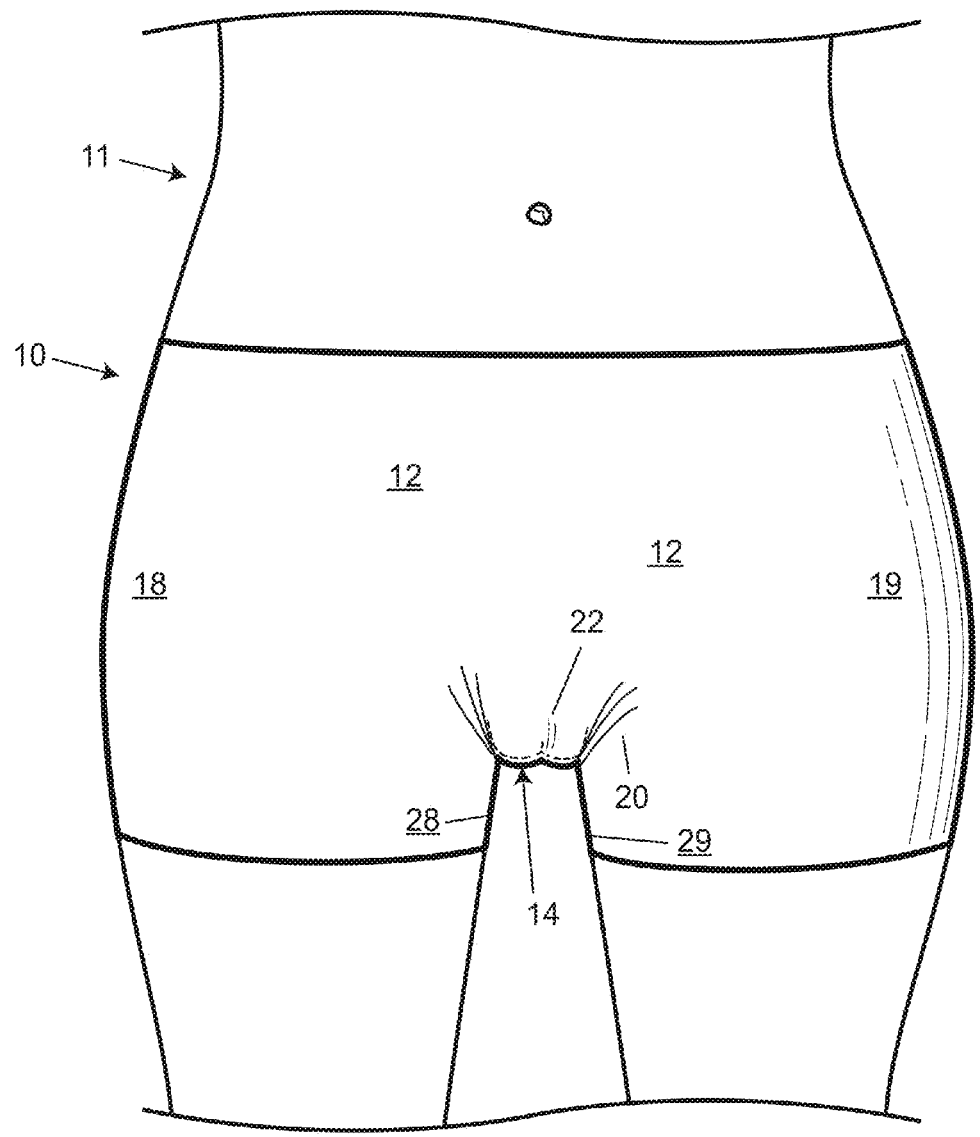
FIG. 2 shows a front view of an embodiment of the present invention disposed on a body's lower torso and upper legs.
Figure 3:
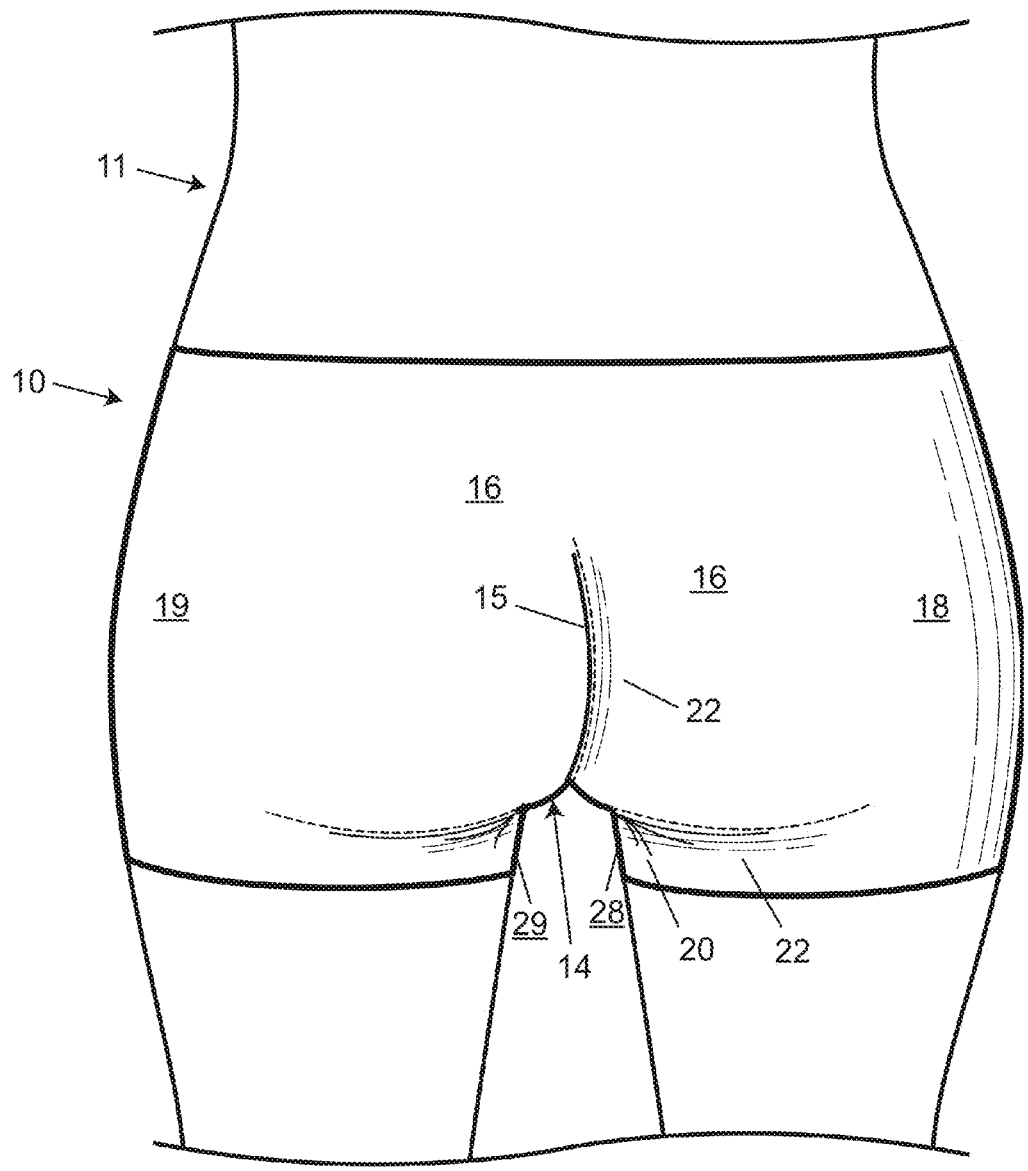
FIG. 3 shows a rear view of an embodiment of the present invention disposed on a body's lower backside and upper legs.
Figure 4A:
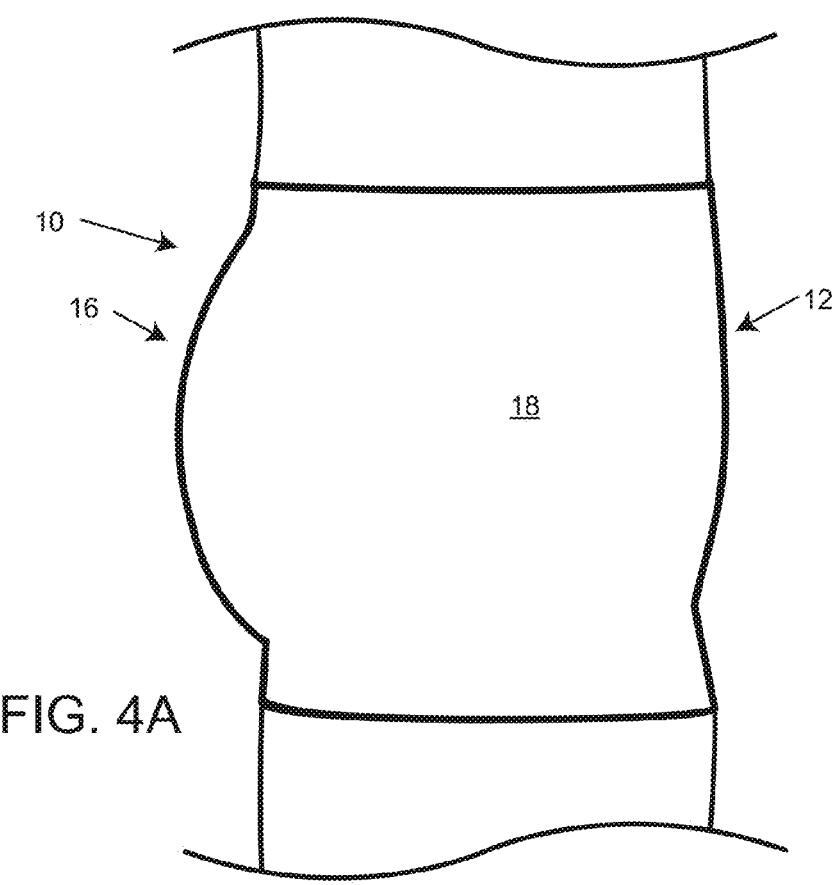
FIG. 4A shows a side view of an embodiment of the present invention disposed on a body's right lower torso and upper leg.
Figure 4B:
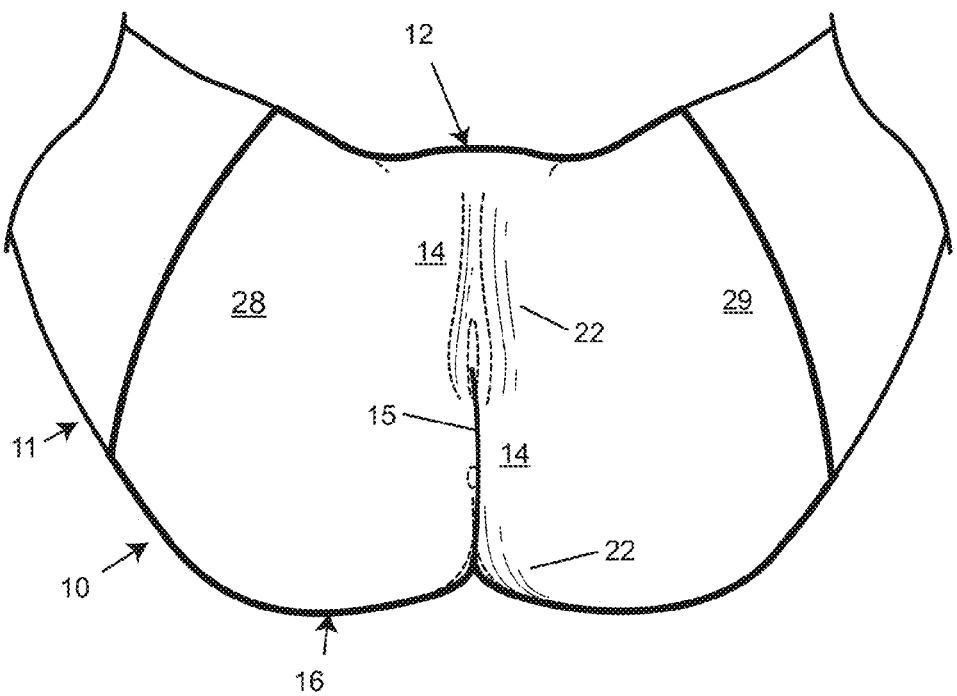
FIG. 4B shows a caudal view of an embodiment of the present invention.

An embodiment of the barrier is illustrated in FIGS. 1A, 1B, 1C. FIG. 1A is a front view of an embodiment, and FIG. 1B is a rear view of the embodiment. The barrier, generally designated 10, is configured in the overall shape of an undergarment. Barrier 10 includes a front portion 12, a genital portion 14, and a back portion 16. In this embodiment, genital portion 14 and back portion 16 include a crease 15. This embodiment also includes thigh portions 18 and 19, which are each connected to front portion 12 and to back portion 16. FIG. 1C is a left view of the embodiment folded such that back portion 16 and front portion 12 are touching.

An embodiment of barrier 10 is illustrated in FIG. 2, FIG. 3, and FIGS. 4A to 4B, in front, rear, side, and caudal views, respectively. In FIG. 2, FIG. 3, and FIGS. 4A, 4B, barrier 10 is being worn by a wearer or body or receiver 11, depicted here as female. Wearer 11's sexual partner is described herein as the "performer" of oral sex. In FIG. 2, FIG. 3, and FIGS. 4A, 4B, front portion 12 extends from the vicinity above wearer 11's pelvis downward and meets with genital portion 14. Genital portion 14 covers wearer 11's vulva, perineum, anus, and groin and extends to back portion 16. Back portion 16 covers wearer 11's buttocks. In some embodiments, inner-thigh portions 28 and 29 extend down the wearer's inner thighs at least 2 mm and as far as knee-length, in order to anchor the barrier in place, to prevent skin-to-skin contact between the performer and the wearer's thighs, and to provide for extra material that can slide up the inner thighs to allow penetration beyond the elastomeric capabilities of the material.

Figure 5A:
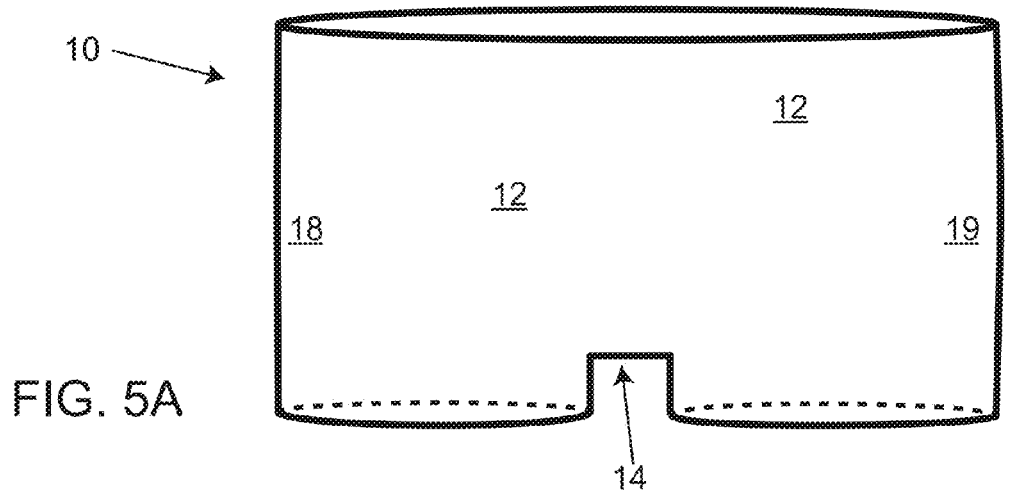
FIG. 5A shows a front view of an embodiment of the present invention.
Figure 5B:
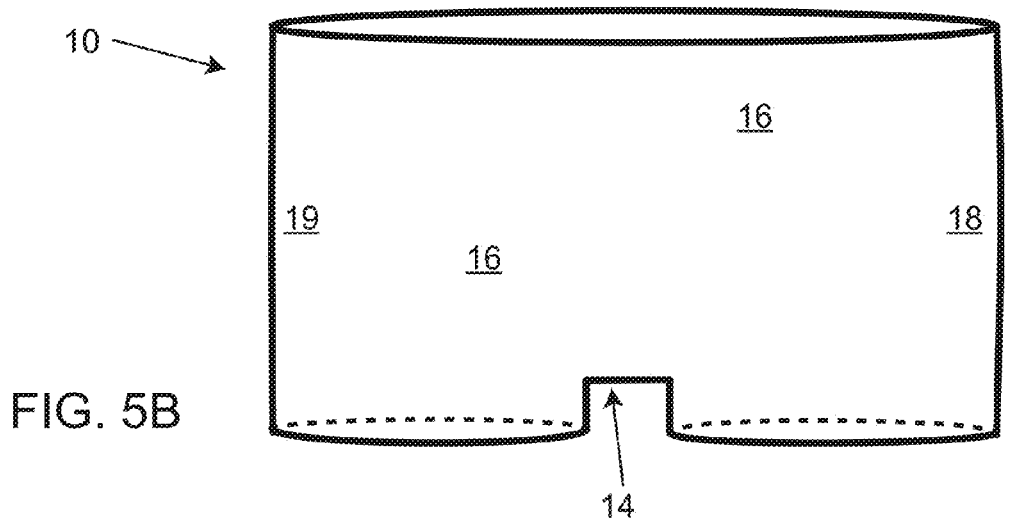
FIG. 5B shows a rear view of an embodiment of the present invention.
Figure 5C:
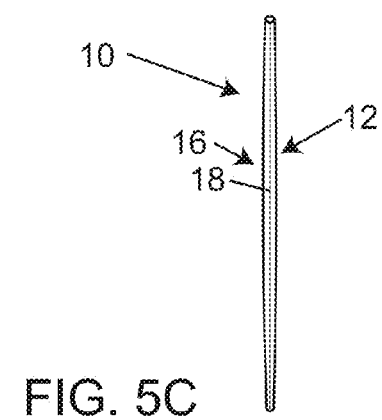
FIG. 5C shows a left side view of an embodiment of the present invention folded such that the back portion and the front portion touch.
Figure 6:
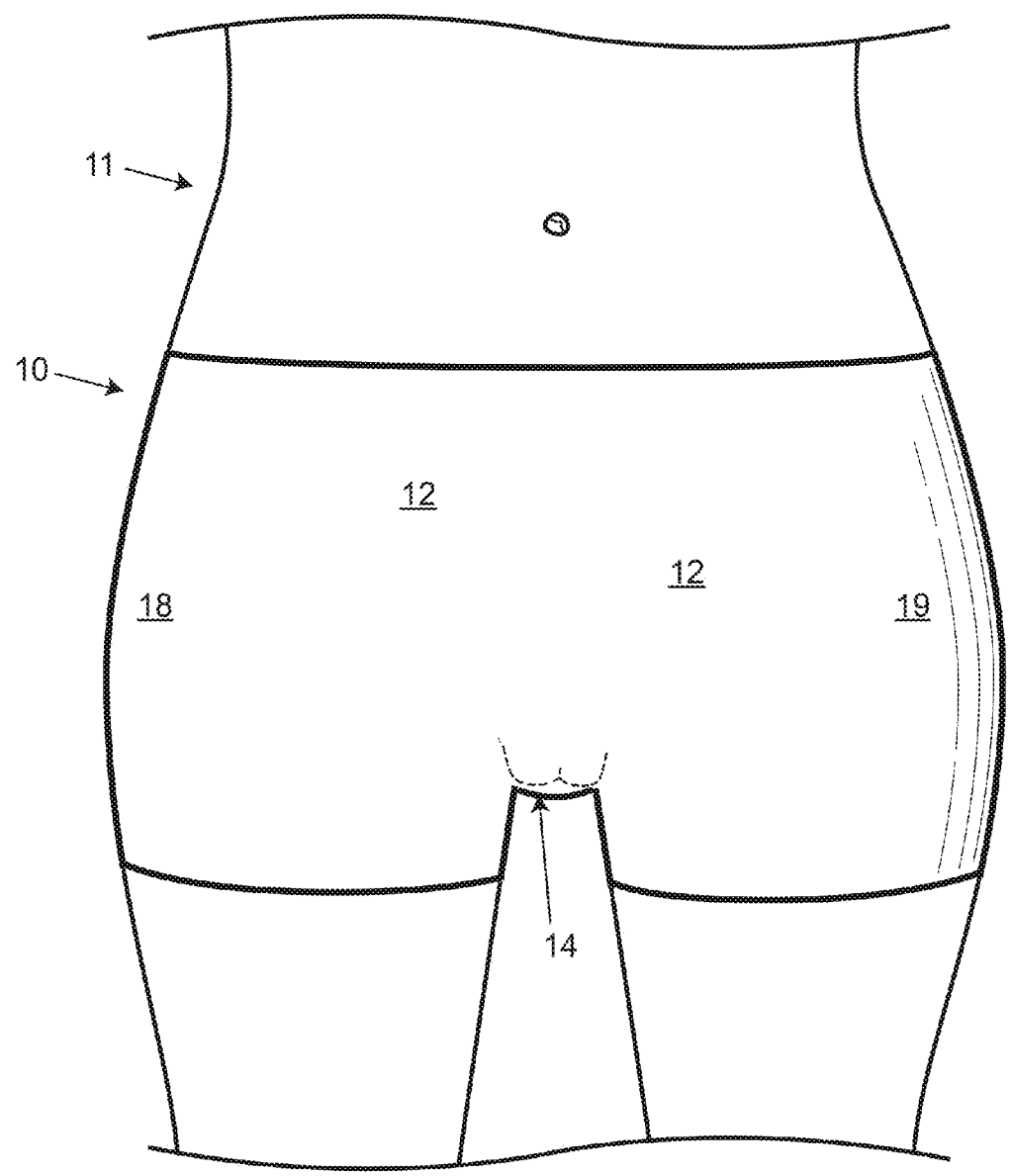
FIG. 6 shows a front view of an embodiment of the present invention disposed on a body's lower torso and upper legs.
Figure 7:
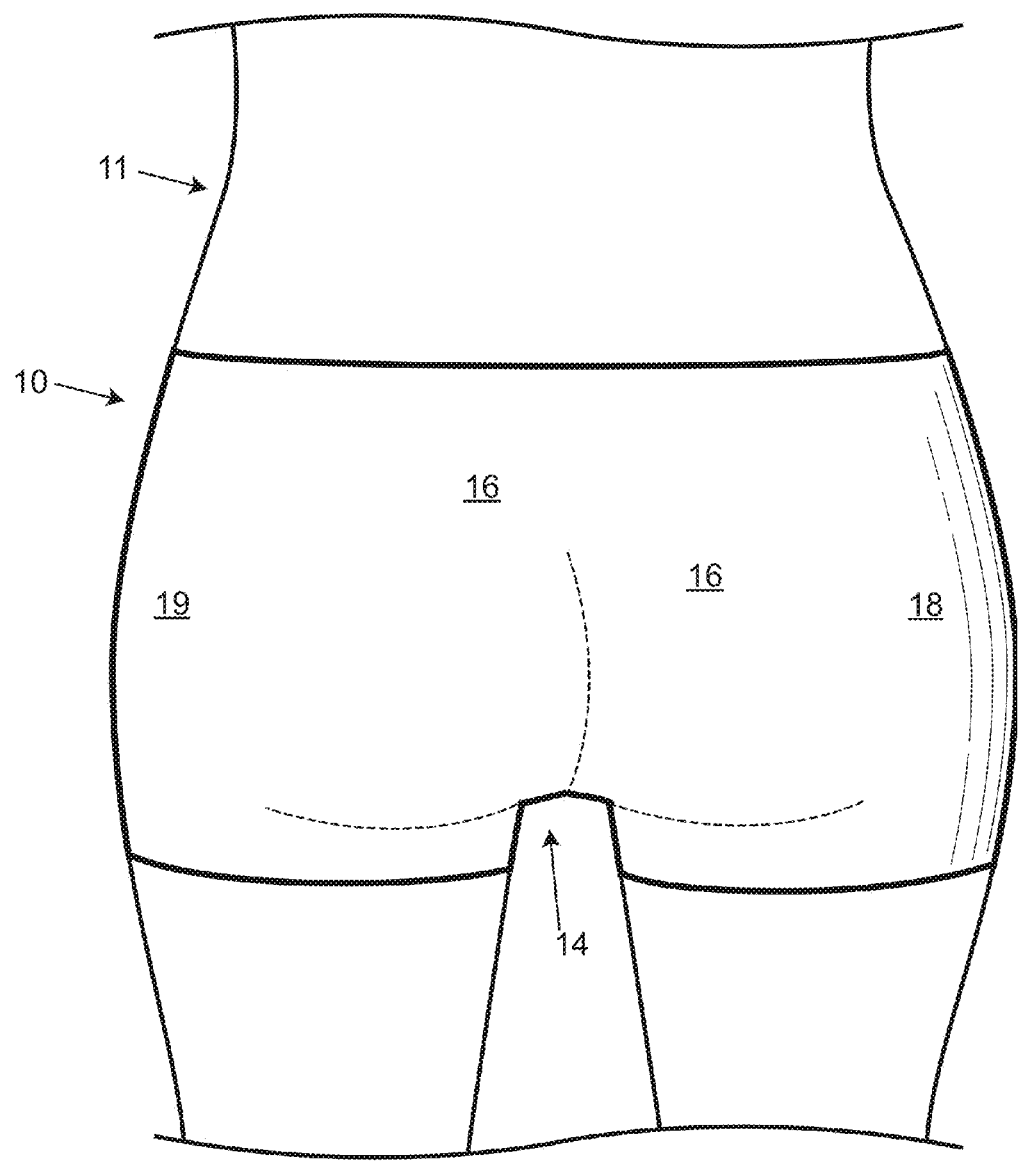
FIG. 7 shows a rear view of an embodiment of the present invention disposed on a body's lower backside and upper legs.
Figure 8A:
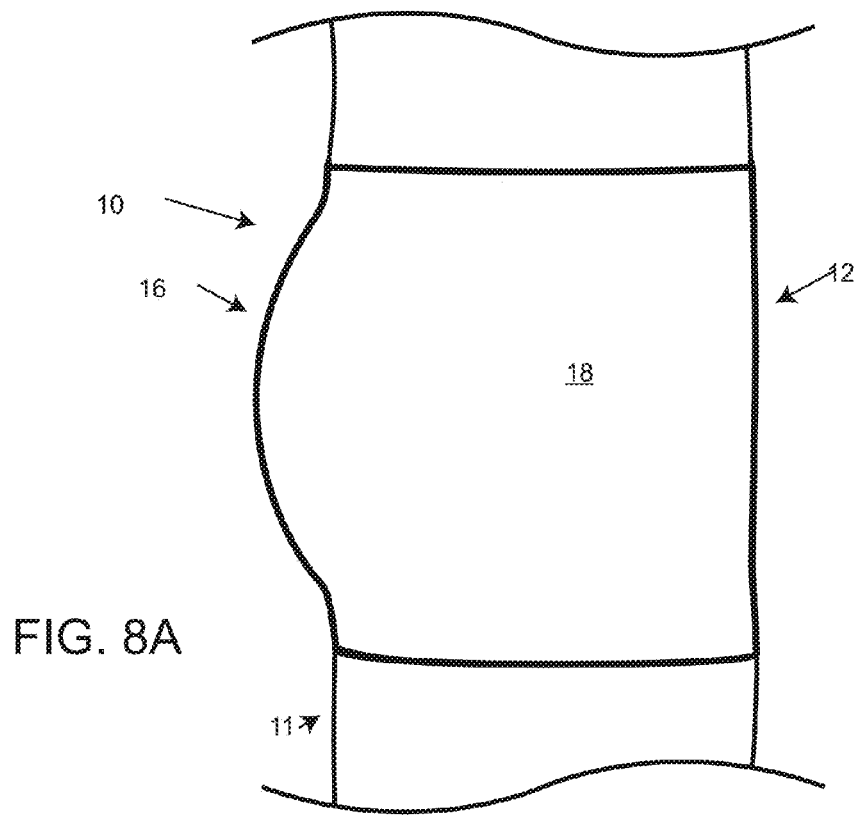
FIG. 8A shows a side view of an embodiment of the present invention disposed on a body's right lower torso and upper leg.
Figure 8B:
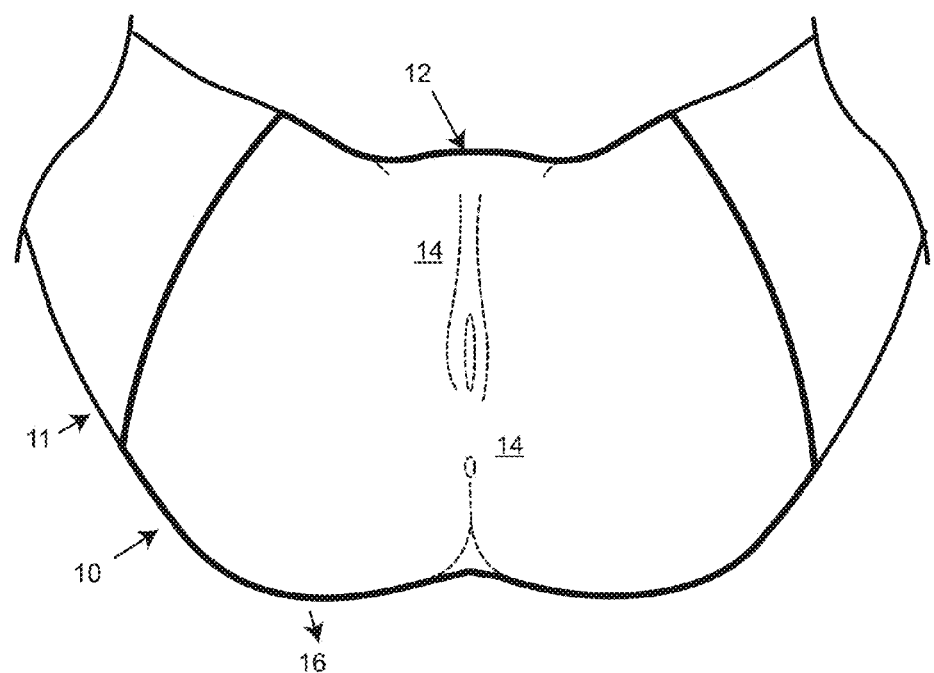
FIG. 8B shows a caudal view of an embodiment of the present invention.
Figure 10A:
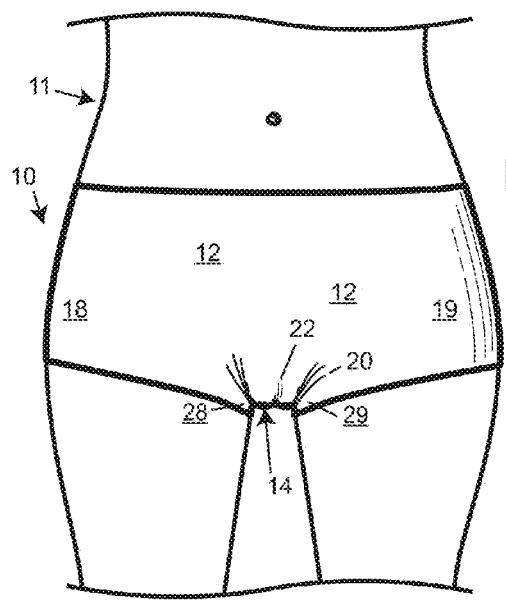
FIG. 10A shows a front view of an embodiment of the present invention disposed on a body's lower torso and upper legs.
Figure 10B:
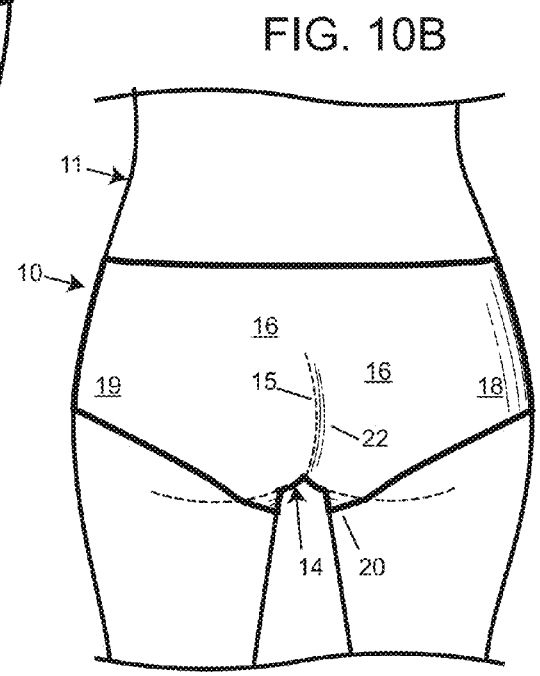
FIG. 10B shows a rear view of an embodiment of the present invention disposed on a body's lower backside and upper legs.
Figure 10C:
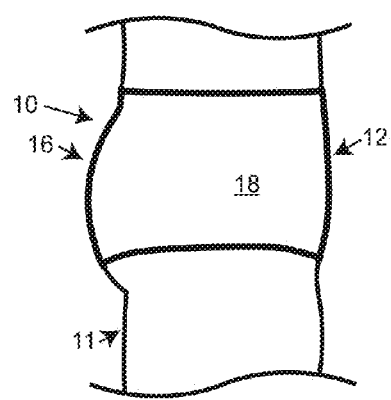
FIG. 10C shows a side view of an embodiment of the present invention disposed on a body's right lower torso and upper leg.
Figure 10D:
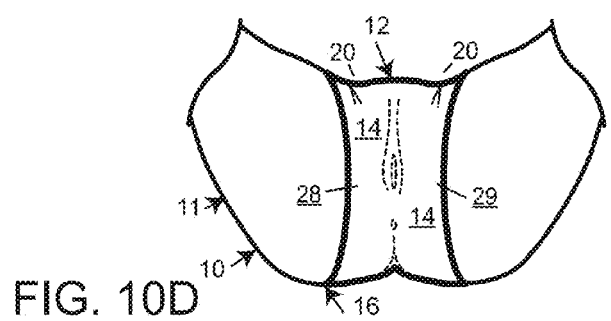
FIG. 10D shows a caudal view of an embodiment of the present invention.

An embodiment of the barrier is illustrated in FIGS. 5A to 5C. FIG. 5A is a front view, and FIG. 5B is a rear view. In this embodiment, genital portion 14 does not include a crease. This embodiment includes thigh portions 18 and 19, which have less curvature than in some other embodiments, and which are each connected to front portion 12 and to back portion 16, which also has less curvature than in some other embodiments. FIG. 5C is a left view folded such that back portion 16 and front portion 12 are touching.

An embodiment of barrier 10 is illustrated in FIG. 6, FIG. 7, and FIGS. 8A, 8B in front, rear, side, and caudal views, respectively. In FIG. 6, FIG. 7, and FIGS. 8A, 8B, barrier 10 is worn by a human wearer 11. In this embodiment, genital portion 14 does not have a crease.

An embodiment of the barrier is illustrated in FIGS. 9A to 9E. FIG. 9A is a front view, and FIG. 9B is a rear view. In this embodiment, the genital portion 14 is wider than in some other embodiments and wider than the genital area of most female humans, and the bottom edges for the legs extend up from the genital portion 14 and out to the thigh portions 18 and 19. FIG. 9C is a left view folded such that back portion 16 and front portion 12 are touching. In the various embodiments illustrated in the Drawings, certain edges 54 in FIGS. 11 to 15 can show different curvatures due to the drafting of the embodiment drawing rather than an indication of a specific curvature. In fact, these edges 54 can be straight, curved, scalloped, etc.

An embodiment of barrier 10 is illustrated in FIGS. 10A, 10B, 10C, 10D, in front, rear, side, and caudal views, respectively. In FIGS. 10A to 10D, barrier 10 is being worn by a wearer 11. In this embodiment, the genital portion 14 is wider than in some other embodiments, and when placed on the body the outside edges of genital portion 14 form inner-thigh portions 28 and 29. The bottom edges for the legs extend up from the genital portion 14 and out to the thigh portions 18 and 19. In an embodiment, the outside edges of the genital portion 14 forming inner-thigh portions 28 and 29 provide for some slight or small excess material to gather on each of the outer sides of the labia adjacent to the wearer's inner thigh. In an embodiment, it is possible that a very slight excess or a crease will form in the inner labia when some wearers don the barrier 10—but this very slight excess is much less than the slight excess material gathering at the outside edges of the genital portion 14. This slight excess material allows for the excess material of the genital portion 14 to move slightly in response to small penetrations or touching in the vaginal or inner labia regions of a wearer, without exposing portions of the outer and/or inner labia. For example, in this embodiment, the excess material does not leave the outer sides of the labia unless there is a vaginal or inner labia penetration or touching necessitating a movement of the slight excess material as the material stretches to accommodate the penetration or touching. In an embodiment, the T-shape barrier shown in FIGS. 9A to 9E, when worn by a person can look like FIGS. 10A to 10D. In some embodiments, as shown in FIG. 9D, the top edge is approximately 15 inches wide and has a circumference of approximately 30 inches, the genital portion is approximately 7 inches wide, the garment is approximately 10 inches high when laid flat, and the thigh portion is approximately 6 inches high. In an embodiment similar to FIGS. 9A to 9E and FIGS. 10A to 10D, thigh portions 18 and 19 are shorter, such that the barrier when worn resembles a bikini style. In some embodiments, as shown in FIG. 9E, the top edge is approximately 15 inches wide and has a circumference of approximately 30 inches, the genital portion is approximately 7 inches wide, the garment is approximately 10 inches high when laid flat, and the thigh portion is approximately 2 inches high.

Figure 12:
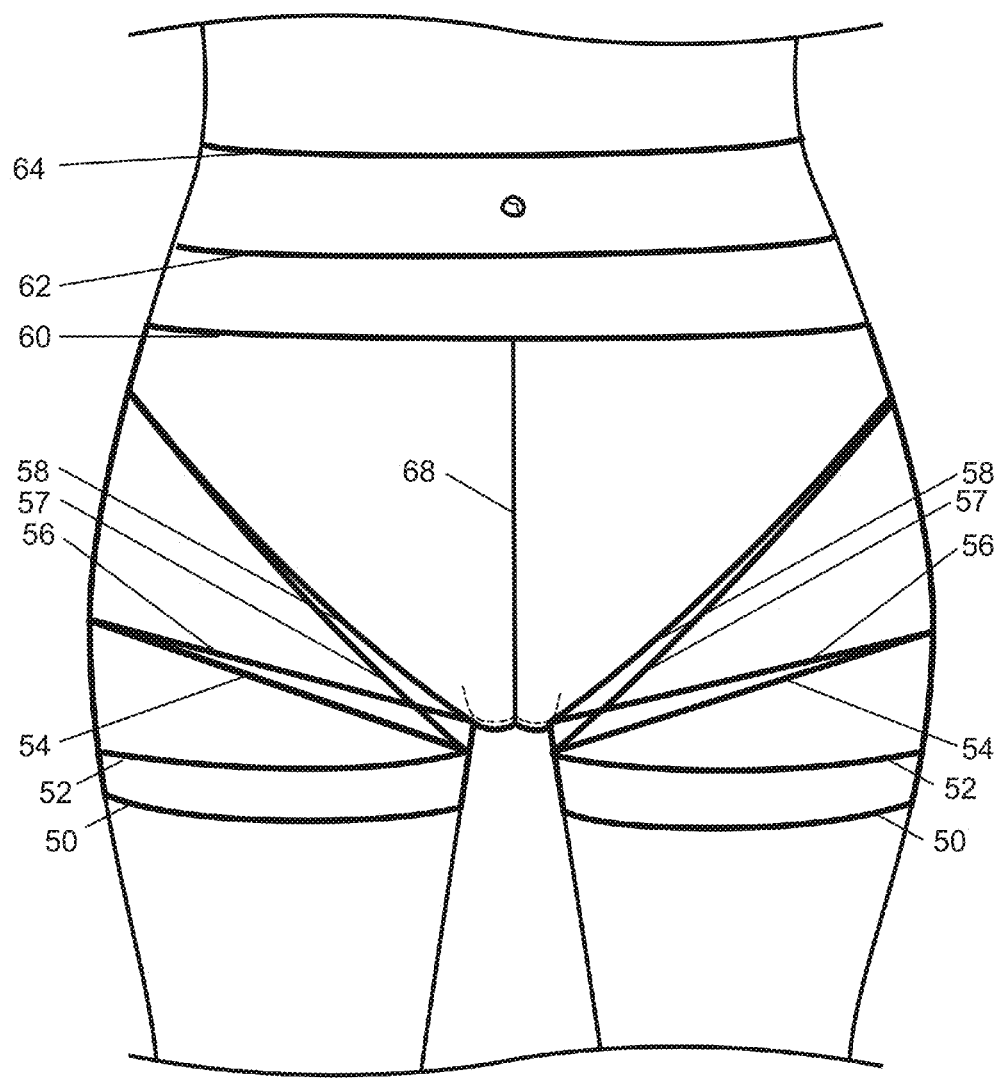
FIG. 12 shows a front view of multiple embodiments of the present invention as worn on a body.
Figure 13:
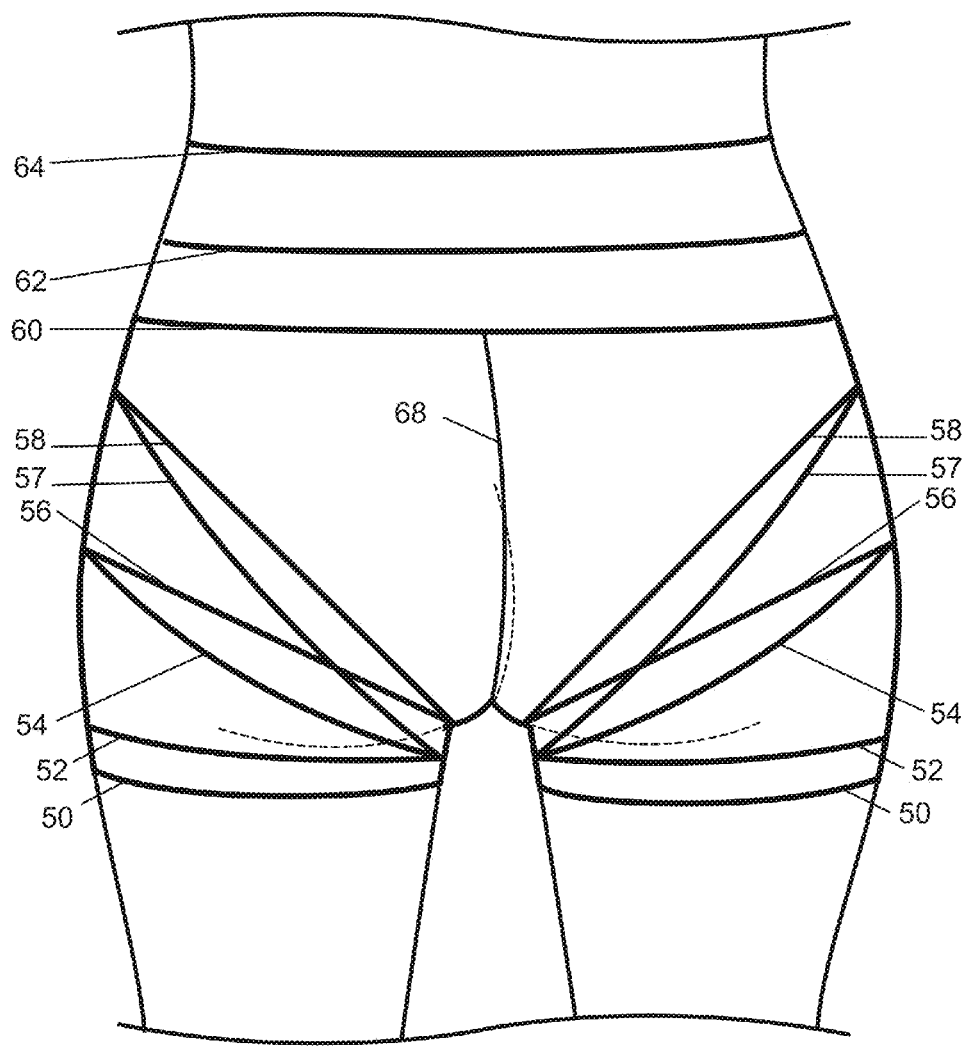
FIG. 13 shows a rear view of multiple embodiments of the present invention as worn on a body.

One feature of embodiments of the barrier including bottom edges (e.g., bottom edges 54) as depicted in FIGS. 9A to 9E, FIGS. 10A to 10D, FIGS. 11C, 11H, FIGS. 14A and 14B, and FIGS. 15A to 15C, or bottom edges 57 as depicted in FIG. 11G, FIG. 12, and FIG. 13, is that the material along the groin portion 14 gathers in useful ways on different bodies—on some bodies the material gathers into wrinkles, and on other bodies the material rests along the inner thighs—and the material along the groin portion 14 can be moved inward on the groin to allow additional penetration into the vagina, beyond what is possible from the material's elastomeric qualities.

Some embodiments cover more or less surface area than other embodiments, as shown in FIGS. 11A to 11H, FIG. 12, and FIG. 13. Some embodiments have bottom edges 50 that extend several centimeters down the thighs and are parallel to the ground, bottom edges 52 that extend only a few centimeters or millimeters down the inner thighs and are parallel to the ground, or bottom edges 54 or 57 that extend only a few millimeters down the inner thighs and extend up on the outer thighs. Other embodiments do not cover the inner thighs and have bottom edges 56 or 58 that extend from each side of the genital portion to the sides of the waist in a boy-short (56) or bikini (58) style. Any of these embodiments could have top edges 60, 62, or 64 that extend to various heights of a body's torso and backside. FIGS. 11A to 11H show various embodiments of the barrier including an assortment of top edges 60, 62, or 64 and bottom edges 50, 52, 54, 56, 57, and 58. The embodiment depicted in FIG. 11H also includes seam 68.

Figure 14A:
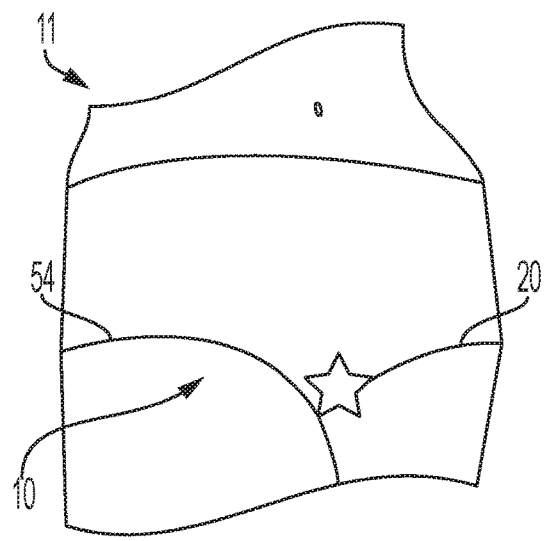
FIG. 14A shows a front view of an embodiment of the present invention.
Figure 14B:
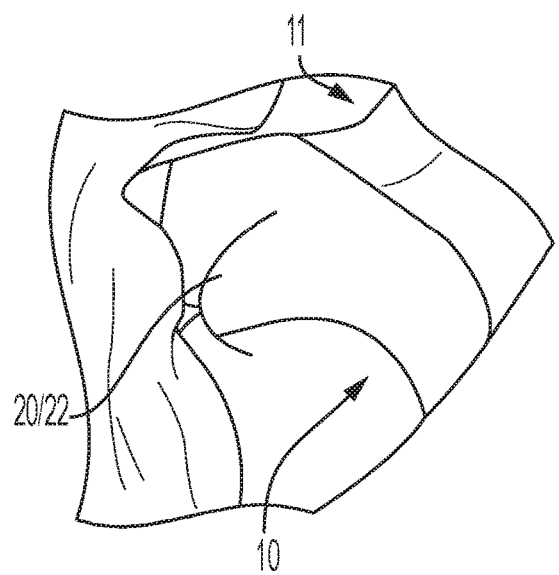
FIG. 14B shows a rear view of an embodiment of the present invention.
Figure 15A:
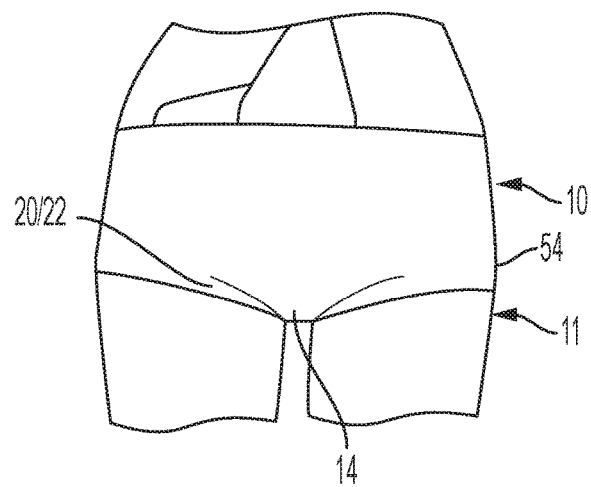
FIG. 15A shows a front view of an embodiment of the present invention.
Figure 15B:
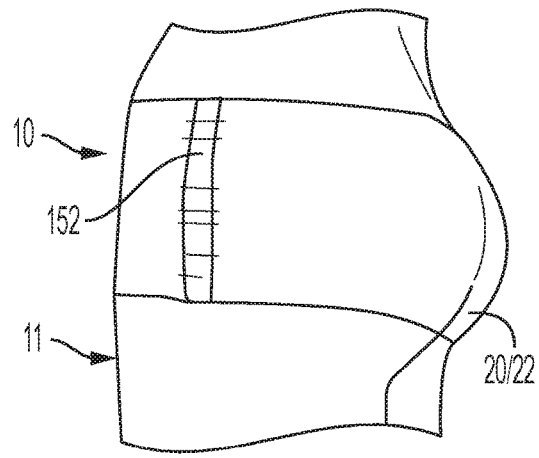
FIG. 15B shows a right side view of an embodiment of the present invention.
Figure 15C:
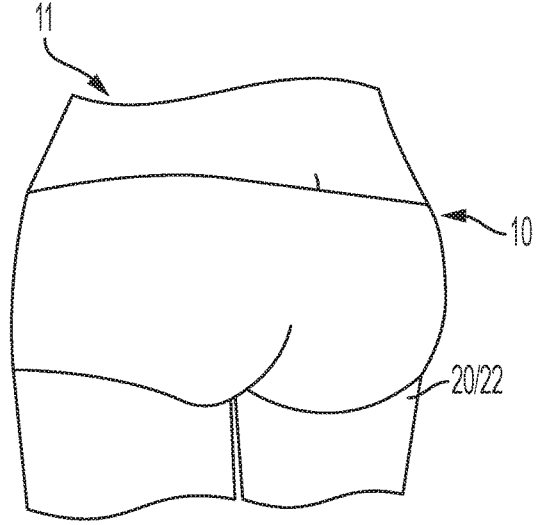
FIG. 15C shows a rear view of an embodiment of the present invention.

FIGS. 14A to 14B and FIGS. 15A to 15C show photographs of an embodiment including the bottom edges 54 depicted in FIGS. 9A to 9E and FIGS. 10A to 10D. On a female human wearer, FIG. 14A shows a front view (redacted for modesty), and FIG. 14B shows a rear view. FIG. 15A shows a front view, FIG. 15B shows a right side view, and FIG. 15C shows a back view, of an embodiment as worn on an (anatomically female) mannequin.

In an embodiment, all portions, including genital portion 14, are configured to fit tightly to the body, both at rest and while engaging in sexual activity. Genital portion 14 contours the body, unlike conventional barriers, for several reasons. First, the aesthetics of sexual activity are very important in maintaining arousal, particularly among partners who may be distracted by concern regarding STIs. Sexual partners utilizing a prophylactic want to view the body-contouring look of many contemporary fashions. Some embodiments so tightly contour the body that wrinkles 20 are created by folds of the material and shadows 22 are created by the barrier's contour of the wearer's anatomy, as in FIG. 2, FIG. 3, FIGS. 4A to 4B, FIGS. 10A to 10D, FIGS. 14A to 14B, and FIGS. 15A to 15C. In an embodiment, for example, those wrinkles 20 and shadows 22, while most likely to appear on the creases between the inner thighs and the genital region and under the curves of the buttocks, will appear in different locations when worn by wearers of different shapes and sizes. Also, some embodiments, such as that depicted in FIG. 6, FIG. 7, and FIGS. 8A, 8B, do not have wrinkles 20 or shadows 22. Also, genital portion 14 fits snugly such that in most cases only one layer of material—rather than additional layers created by the folding of excess material, such as a long protrusion—exists between the performer and the wearer. If additional layers created by the folding of excess material are present, they could diminish sensation for the wearer and prevent breathing and cause gagging for the performer. Furthermore, the excess material could allow bacteria from the anus to reach the vaginal cavity. In some embodiments, the sides of the garment provide for a friction between the material of the garment and the wearer's hips and/or thighs. The friction or resistance to movement allows for better staying ability on the wearer, so that the garment does not move or shift significantly during activity, while preventing the necessity of tight or uncomfortable straps used in other apparatuses to hold dental dams in place. In an embodiment, the friction of the garment against the wearer's body provides a close, stable fit. This can provide a more stable and relatively non-moving garment on the wearer's body, in a comfortable-like manner, so that the material is held in place on the wearer specifically in the genital area, without the addition or use of tight uncomfortable straps or ties.

In an embodiment, barrier 10 is formed of one or more layers, with each layer including one or more substantially impervious material(s) such as natural rubber latex, synthetic latex, latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nanocellulose, superelastomer, vegan material, hypoallergenic material, organic material, other elastomer, other polymer, other copolymer, other polyolefin, and/or a combination of any of these materials. The material can also include additives such as ammonia, water, soap, softening agents, accelerators, anti-oxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives. The barrier 10 is flexible enough for the wearer to comfortably reposition her body; pliable enough to show an outline of the wearer's anatomy for aesthetic appeal and for easy identification by the performer; strong enough to prevent breakage during vigorous use; and of a thickness similar to a conventional condom or a dental dam, to allow the greatest degree of tactile sensitivity and to prevent fatigue of the performer.

In an embodiment, the garment can be one or more layers of an elastomeric material or other flexible-type material such as a moisture-resistant spandex or other textile. In an embodiment, the garment can be composed of more than one type of material in the same garment or layers of the garment. In an embodiment, the garment can include material that is dipped in or otherwise coated in a solution or material. In an embodiment, the garment can include at least one printed pattern. For example, the printed pattern/coloring can be included in the solution, be added as a subsequent solution for dipping, be painted/sprayed on, and/or be added in another available manner to the garment. In some embodiments, items of material known in the fashion arts are attached to the barrier for decorative purposes.

Some embodiments of the barrier have an interchangeable front and back, such that the wearer can quickly put on the garment without determining which side is the front portion and which side is the back portion. For example, the barrier depicted in FIGS. 14A to 14B and FIGS. 15A to 15C has an interchangeable front and back. Other embodiments include a different cut, seam, embellishment, and/or design in the front as compared to the back, such that there is a designated front portion and a designated back portion of the garment. For example, the barrier embodiment depicted in FIG. 11H has a different cut in the front and the back.

In some embodiments of the barrier, color, pattern, scent, and taste are varied, and some embodiments of the barrier are coated with lubricant and/or powder. In an embodiment, the material of the barrier, the powder dusted on the barrier, and/or the lubricant applied to the barrier is scented and/or has a taste. For example, the scent and/or taste can be strawberry, raspberry, any other fruit flavor, chocolate, vanilla, caramel, any other confectionary flavor, bacon, steak, chicken, pistachio, peanut, any other food flavor, spearmint, peppermint, sage, any other herb flavor, and/or any other flavor known in the art. For example, the scent and/or taste can be organic/vegan.

Figure 16A:
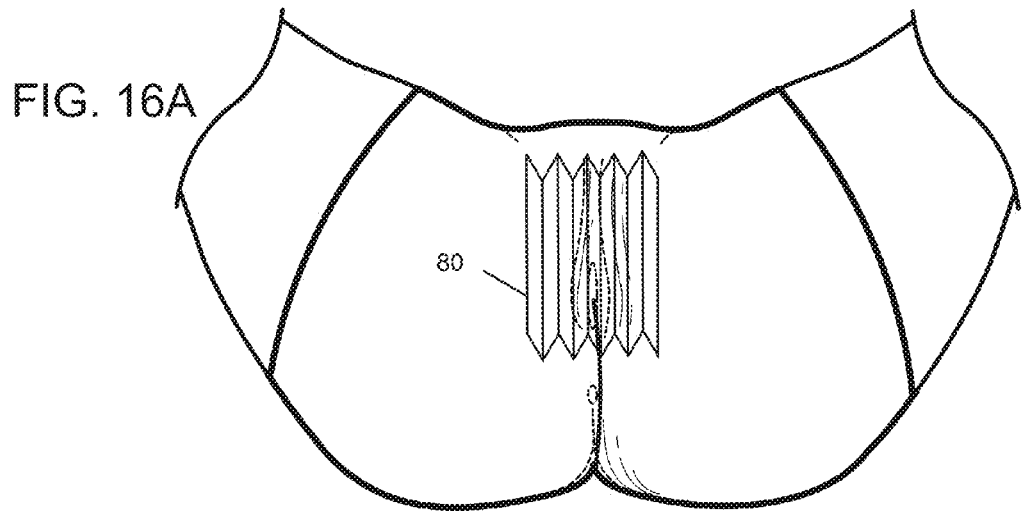
FIG. 16A shows a caudal view of an embodiment of the present invention having pleats in the vulval area.
Figure 16B:
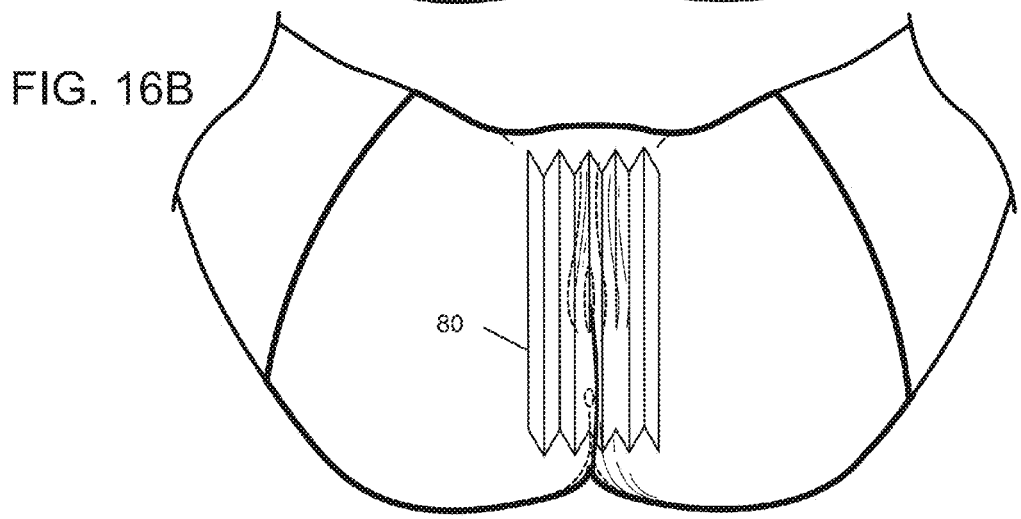
FIG. 16B shows a caudal view of an embodiment of the present invention having pleats in the vulval and anal area.
Figure 16C:
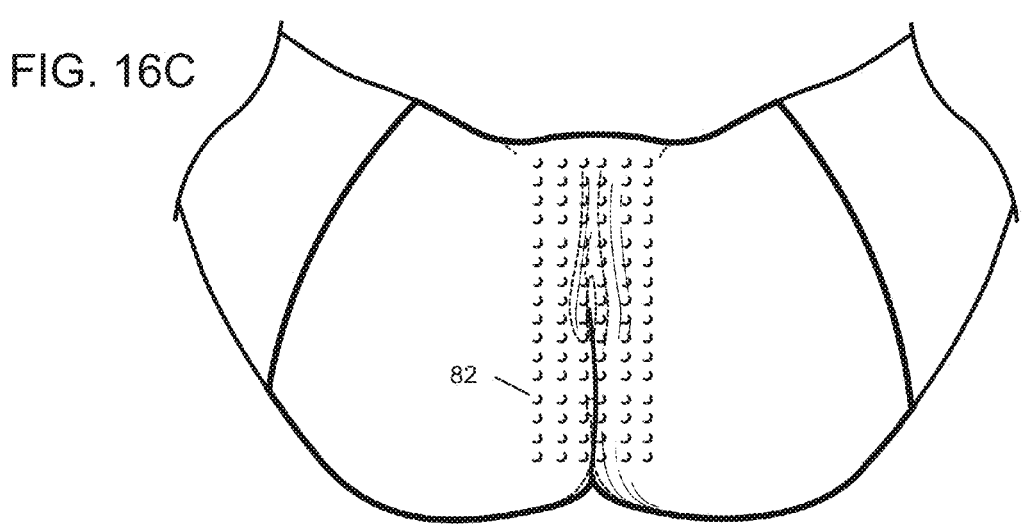
FIG. 16C shows a caudal view of an embodiment of the present invention having texture beads.

Some embodiments include texture to increase sensation, such as (but not limited to) the accordion folds 80 depicted in FIG. 16A over the vulva and FIG. 16B over the full genital region and the texture beads 82 depicted in FIG. 16C (which, in addition to providing texture, can also decrease the wearer's insecurity regarding bumps that are characteristic of STI outbreaks). In some embodiments, creases and/or seams such as crease or seam 68, as depicted in FIG. 12 and FIG. 13—or the shorter crease 15 as depicted in FIGS. 1A to 1C, FIG. 3, and FIGS. 4A to 4B—increase sensation through texture and allow greater access for the performer to the area between the wearer's right and left labia majora and to the anus and perineum. Some embodiments include texture or cut-outs in a "figure eight", a swirl, an alphanumeric symbol, a heart, a logo, a brand name, a brand initial, and/or another shape, either as a decorative element, to keep the garment in place, and/or to instruct the performer where to move their tongue. Some embodiments include other textures including bumps, ruched material, et al. Some embodiments include lubricant, cooling lubricant, warming lubricant, cooling liquid, and/or warming liquid to increase sensation.

In some embodiments, the genital region of the garment is manufactured as a wider area than that of fashion undergarments, to allow different uses. In some embodiments, the genital region of the garment is manufactured as a wider area to allow for less pulling of garment material away from the thigh regions or the sides of the genital region. In some embodiments, as the garment with a wider area is pulled up over the legs, the material on the sides of the genital region will drag along the inner thighs; on some users that material will rest into place on the top of the inner thighs, and in other users that material will gather on the sides of the genital region, i.e., between each outer labia and its adjacent leg. Due to this excess width, while oral sex is being performed on a wearer of such an embodiment, the material that sits at the inner thighs and/or on the sides of the genital region can move slightly in response to vaginal penetration by a tongue, fingers, or other objects without exposing portions of the outer and/or inner labia, as would a garment with a genital region having the width of fashion undergarments. In an embodiment, material can gather slightly between a left outer side of the labia and the respective adjacent left thigh region, and/or between a right outer side of the labia and the respective adjacent right thigh region. For example, in this embodiment, the material does not gather in the inner labia and/or vaginal area unless, or gathers only minimally in the inner labia and/or vaginal area until, the user effects a vaginal or other penetration or touching which necessitates the movement of the slight material excess as the material stretches due to such penetration or action.

In an embodiment, the outer edges of the thigh regions and/or the torso region are a smaller circumference to enforce an effective seal or closure to prevent fluids from escaping during use.

In some embodiments, the top edges are straight across the waist or hips. In some embodiments, the top edges are scooped in the front and/or the back such that the thigh portions extend higher than the middle portion and/or the back portion. This scooping can be achieved through cutting, die-cutting, excising, or any other method known in the art. In some embodiments, other functional and/or design options are available for the top edges or the bottom edges, including a downward diamond cut, scalloped cuts, fringing, and so forth. Likewise, after the manufacturing of the barrier garment, in embodiments, additional embellishments can be glued, heated, or attached to the barrier garment including lace, spandex, cotton, and other materials for aesthetic and/or functional purposes. For example, different material can be added to the barrier garment in order to increase the usability, design, and/or aesthetic of the barrier garment for a different texture or a handle device to pull on the barrier garment.

Some embodiments have bottom edges 50, 52, 54, 56, or 58 and/or top edges 60, 62, or 64 that are rolled, reinforced, sewn, heated, cut, multi-layered, sealed, and/or manufactured in another way so as to provide additional strength to the edges and, in some embodiments, to prevent ingress and/or egress of fluids. Some embodiments have bottom edges 50, 52, 54, 56, 57, or 58 and/or top edges 60, 62, or 64 that are tighter than the remainder of the barrier. Some embodiments have bottom edges 50, 52, 54, 56, 57, or 58 and/or top edges 60, 62, or 64 that are cut in a decorative manner, for example scalloped, fringed, or any other manner known in the art.

Figure 17:
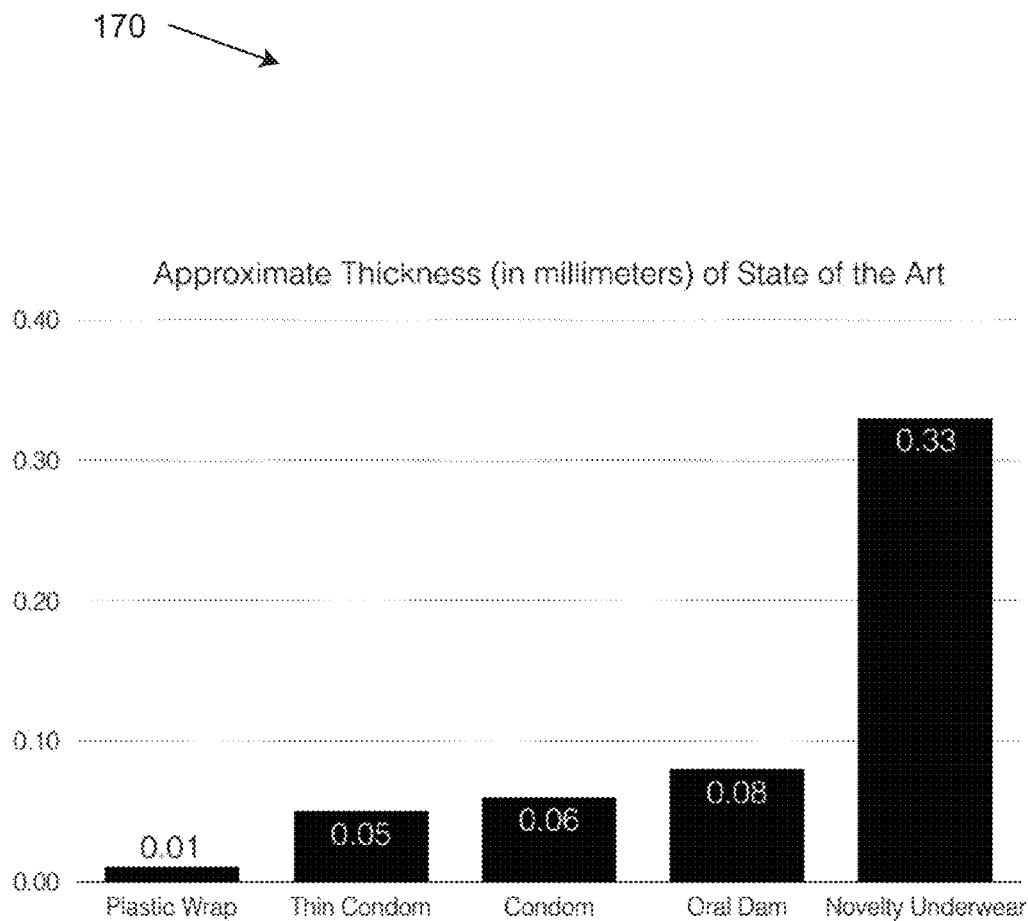
FIG. 17 shows a chart illustrating a comparison of thicknesses of the state of the art.

The thickness of the barrier is varied in some embodiments. FIG. 17 shows a chart 170 that depicts the thickness (in millimeters) of the state of the art. The thickness of novelty rubber underwear, at 0.33 mm or thicker, is more than four times thicker than an oral dam, more than five times thicker than a condom, and more than six times thicker than a thin condom. As a result, the novelty rubber underwear transfers substantially less sensation from the performer's side to the recipient's side, causing a less-pleasurable sexual experience. In some embodiments, the barrier has a thickness comparable to a thin condom, condom, and/or oral dam and therefore is substantially thinner than novelty rubber underwear. The barrier embodiment is extremely thin when held up by a hand, and it drapes down gracefully. The barrier embodiment curves along the anatomy of the hand. The barrier responds similarly when placed on a genital region.

Figure 18:
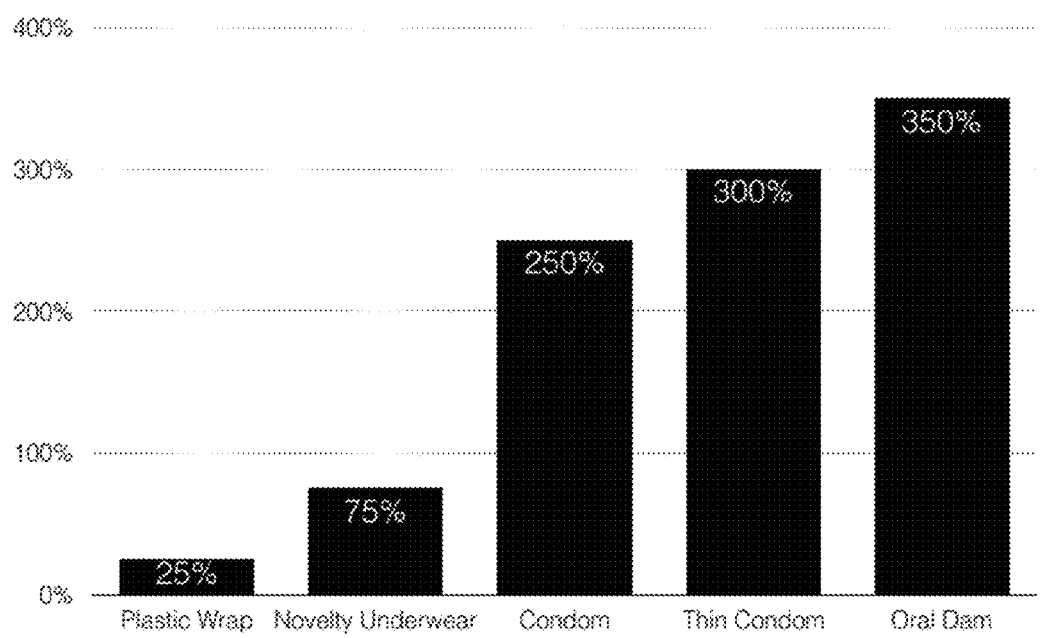
FIG. 18 shows a chart illustrating an approximate expandability of the state of the art.

Some embodiments have more expandability than other embodiments. For example, FIG. 18 contains chart 180 that depicts the expandability of the state of the art. The condom, thin condom, and oral dam have expandability of 250-350%, or more, of their length at rest. (For example, a 10 mm piece of a thin condom will stretch to 40 mm.) Plastic wrap and novelty rubber underwear are significantly less expandable. In some embodiments, the barrier has an expandability comparable to a condom, thin condom, and/or oral dam.

In an embodiment, the barrier responds to the application of pressure by expanding, though it need only be expandable enough to fit slightly-different sized wearers and to allow insertion of a tongue. In an embodiment, the barrier is manufactured in a range of sizes, reducing the need for expandability of the material. In another embodiment, the barrier is sufficiently expandable such that a single barrier can expand to fit wearers of most shapes and sizes.

In an embodiment, the barrier is donned before sexual activity takes place, either immediately before or as an undergarment worn for non-sexual activity. To don the barrier, one leg of the wearer is inserted in each of the spaces between the genital portion and the thigh portions, with the front portion facing forward. If desired, a lubricant can be applied inside the barrier for ease of donning and to increase sensation for the wearer. A performer then contacts the exterior portion of the membrane with their tongue, mouth, nose, fingers, and/or other small protuberances. After use, the device is pulled off or rolled downward off the wearer.

Figure 19:
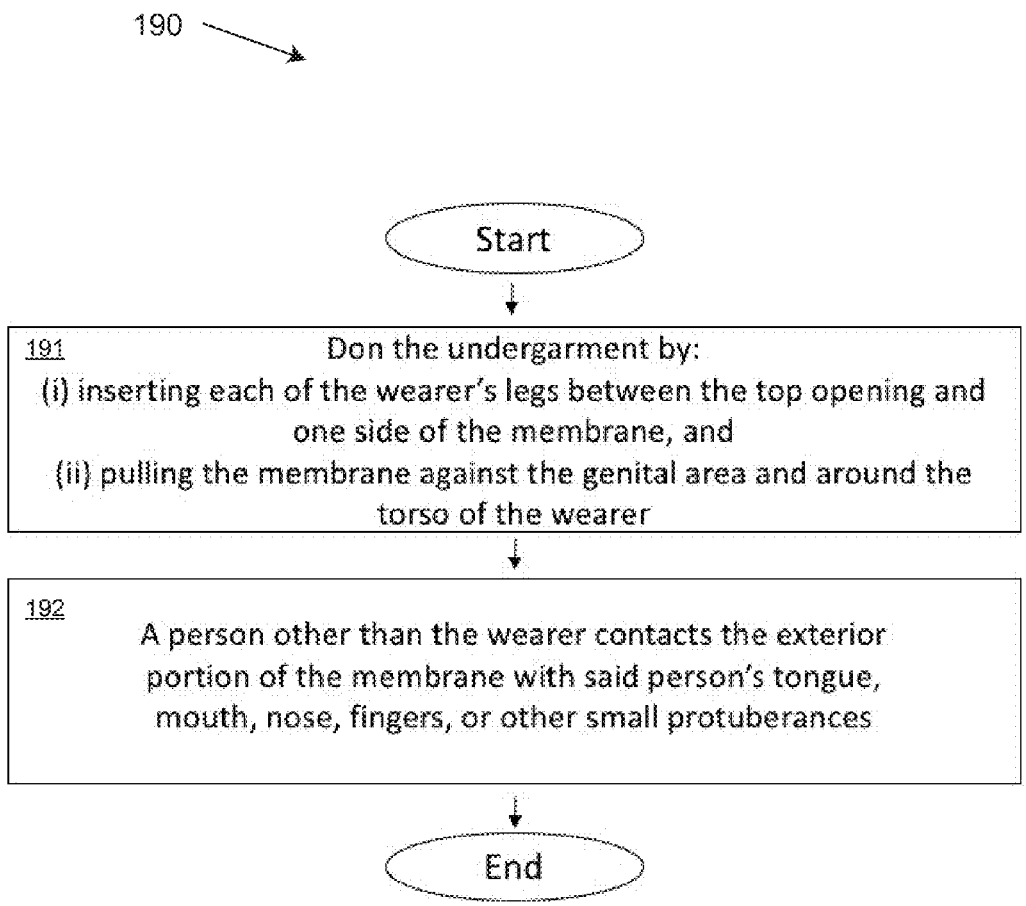
FIG. 19 shows a flow chart illustrating a method of using an embodiment of the present invention.

As process 190 depicted in FIG. 19 shows, a method of oral-sexual relations includes:

Step 1 (191): Don the undergarment by: (i) inserting each of the wearer's legs between the top opening and one side of the membrane, and (ii) pulling the membrane against the genital area and around the torso of the wearer.

Step 2 (192): A person other than the wearer contacts the exterior portion of the membrane with said person's tongue, mouth, nose, fingers, or other small protuberances.

Figure 27:
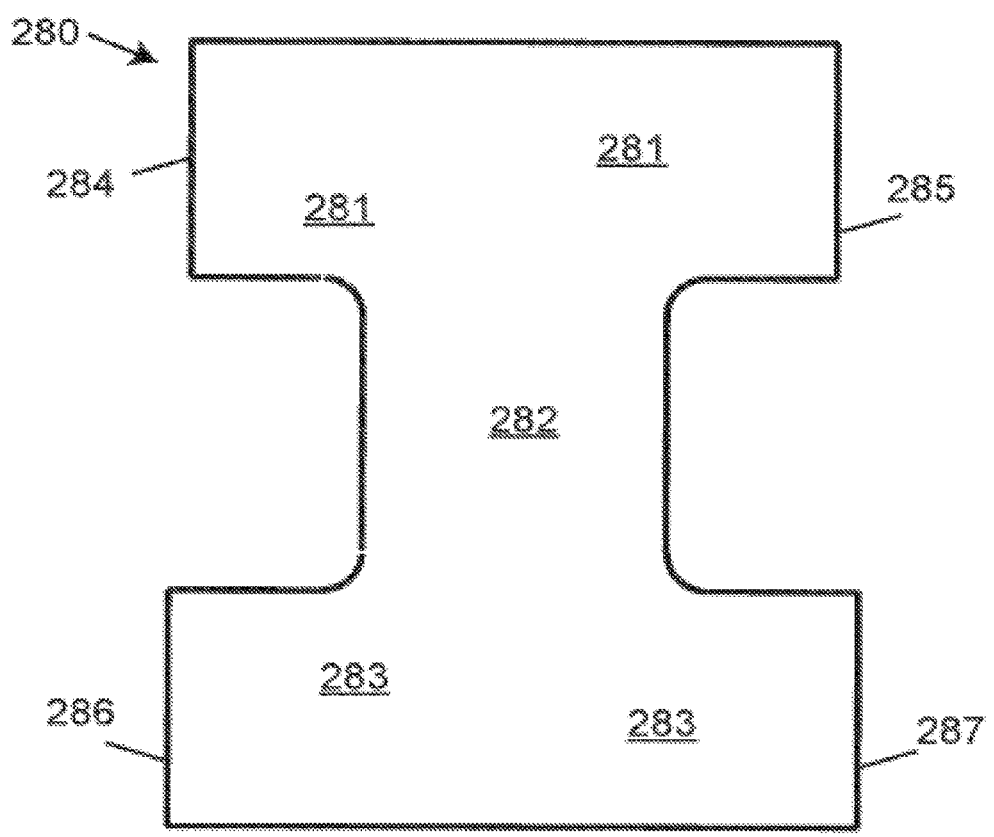
FIG. 27 shows a top view of a pattern used for manufacturing a garment embodiment of the present invention.

In some embodiments, the barrier is formed by cutting a sheet of material in a pattern and creating seams 152 to connect portions of said material. Seams can be created using adhesive, liquid latex, UV-cured adhesive, tape, glue, thread, or any method known in the art. In some embodiments, said seams 152 can be located on the sides of the thighs (e.g., as shown in FIG. 15B), in the genital region of the barrier, and/or in any other location(s) suitable for a seam. FIG. 27 shows a pattern that can be cut into a sheet of material to create an embodiment of the barrier. Front portion 281 connects to genital portion 282, which connects to back portion 283. Side portion 286 is seamed with side portion 284, and side portion 287 is seamed with side portion 285.

Figure 28:
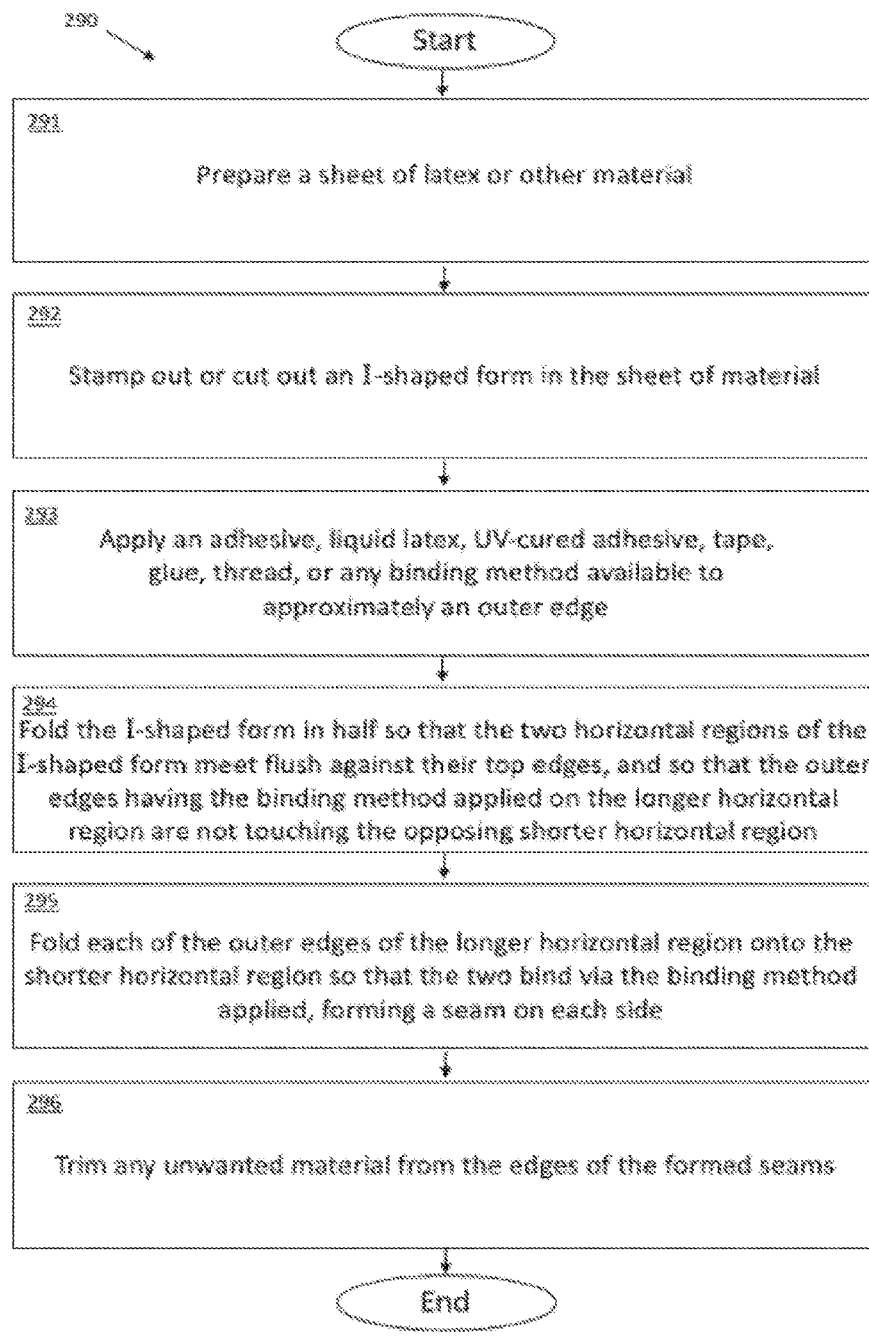
FIG. 28 shows an example method of manufacturing according to an embodiment of the present invention.

FIG. 28 shows an embodiment 290 of a method of manufacturing a barrier garment (for example, one such as that shown in FIG. 29) from a sheet of latex as follows:

Step 1 (291): Prepare a sheet of latex or other material, as described herein, for a barrier garment for use in sexual relations. The sheet of material can be a continuous sheet or roll of material that is extended when needed either manually or via a machine.

Step 2 (292): Stamp out or cut out an I-shaped form in the sheet of material. For example, the stamp out can be by a machine having the shape predetermined. For example, the cut out can be done manually or by a machine to cut away with a blade, laser, or other device, unneeded material from the sheet of material. For example, the I-shaped form can be a variety of different measurements, depending upon the intended wearer or needs. In an embodiment, the I-shaped form has measurements according to those provided in FIG. 9D or FIG. 9E, or, for example, in FIG. 29.

Step 3 (293): Apply an adhesive, liquid latex, UV-cured adhesive, tape, glue, thread, or any binding method available to approximately an outer edge of the garment. In an embodiment, the binding method is applied to only the outer edges of the longer horizontal region. See, e.g., FIG. 29, binding method applied 309, 310.

Step 4 (294): Fold the I-shaped form in half so that the two horizontal regions of the I-shaped form meet flush against their top edges, and so that the outer edges having the binding method applied on the longer horizontal region are not touching the opposing shorter horizontal region.

Step 5 (295): Fold each of the outer edges of the longer horizontal region onto the shorter horizontal region so that the two bind via the binding method applied, forming a seam on each side.

Step 6 (296): Trim any unwanted material from the edges of the formed seams.

Figure 29:
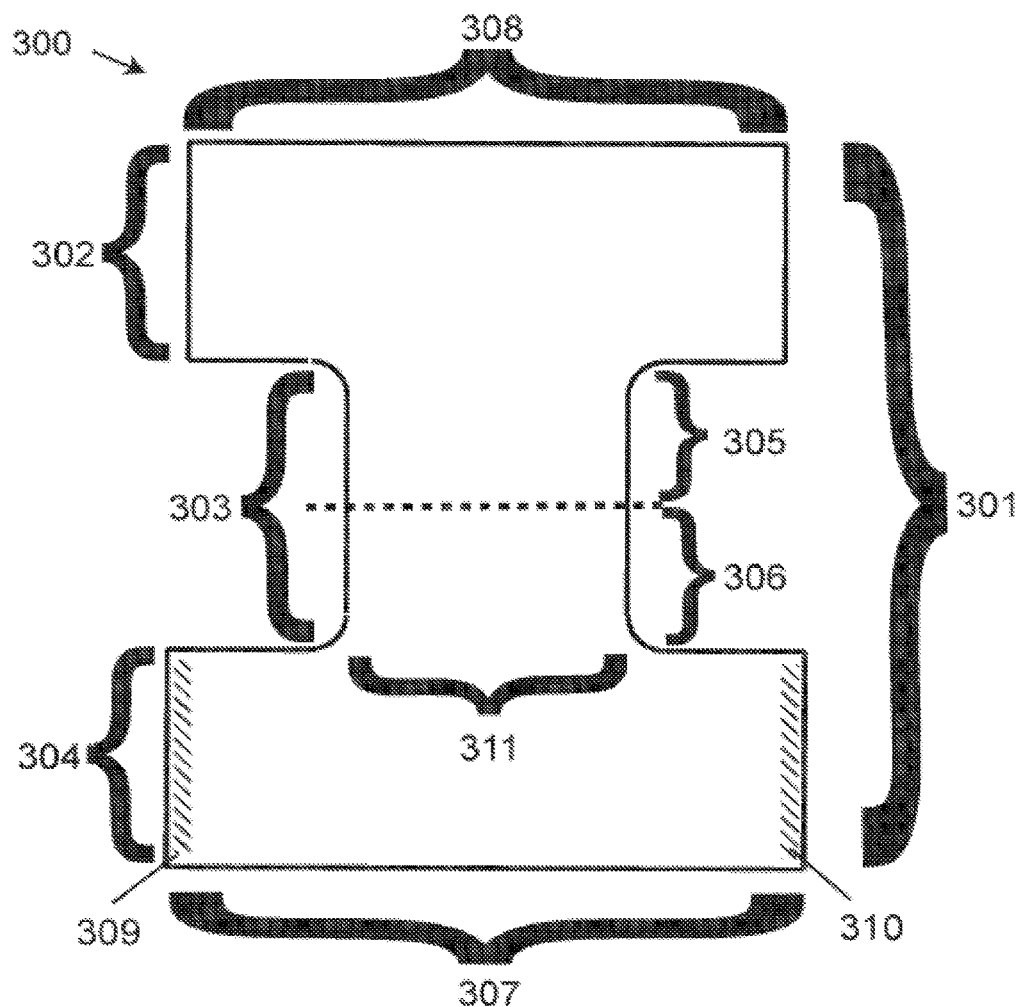
FIG. 29 shows an example garment apparatus.

In FIG. 29, an example garment material is shown in the either stamped out or cut out or made I-shaped form 300. For example, in an embodiment, the measurement of a first horizontal region 308 is of a shorter width than the second horizontal region 307. For example, in an embodiment, the first horizontal region 308 has a width of approximately 15 inches. For example, in an embodiment, the second horizontal region 307 has a width longer than approximately 15 inches. For example, the second horizontal region 307 has an approximate width of 15.5 inches, 16 inches, 17 inches, or longer. In an embodiment, the form 300 has a total length 301 which encompasses the first horizontal region length 302, the vertical region length 303, and the second horizontal region length 304. For example, the form's total length 301 can be approximately 20 inches. For example, the form's total length 301 can be more or less than approximately 20 inches depending upon the size of the intended wearer or of the intended garment. For example, the first horizontal region length 302 and the second horizontal region length 304 are equal in length. For example, the horizontal region lengths 302, 304 are each approximately 6 inches. For example, the horizontal region lengths 302, 304 are each approximately 2 inches. For example, the horizontal region lengths 302, 304 are a size that is useful for a specific type of garment (e.g., boyshort, panty, bikini, et al.). For example, one of the first or second horizontal region lengths 302, 304 is longer in length than the second or first horizontal region lengths 304, 302, respectively. For example, when the first and second horizontal region lengths 302, 304 are different, then, when binding the two horizontal regions as in FIG. 29, for example, the side seams formed on the horizontal region can be ruched seams. The vertical region length 303 is equal in length to the vertical region length 305 plus the vertical region length 306. In an embodiment, the vertical region lengths 305, 306 are equal in length. For example, the vertical region lengths 305, 306 are approximately 4 inches each. For example, the vertical region lengths 305, 306 are approximately 8 inches each. In an embodiment, the vertical region lengths 305, 306 are different in length. For example, the difference in length can be to handle a specific body type or desired fit or aesthetic look. The vertical region width 311 is less than the horizontal region widths 308, 307. For example, the vertical region width 311 is approximately 7 inches. For example, the vertical region width is greater than or less than approximately 7 inches. For example, the vertical width is wider than the gusset of fashion underwear.

In an example, referring to the form of FIG. 29, the first horizontal region width 308 is approximately 15 inches, and the second horizontal region width 307 is more than approximately 15 inches, e.g., approximately 16 inches. The first and second horizontal region lengths 302, 304 are each approximately 6 inches. The vertical region lengths 305, 306 are each approximately 4 inches. The vertical region width 311 is approximately 7 inches.

In an example, referring to the form of FIG. 29, the first horizontal region width 308 is approximately 15 inches, and the second horizontal region width 307 is more than approximately 15 inches, e.g., approximately 16 inches. The first and second horizontal region lengths 302, 304 are each approximately 2 inches. The vertical region lengths 305, 306 are each approximately 8 inches. The vertical region width 311 is approximately 7 inches.

For example, in FIG. 29, the I-shaped garment form 300 shown can be stamped cut or somehow removed from a sheet of material such as latex or other material. A binding material can be applied to the outer edges 309, 310 of at least one horizontal region. The I-shaped garment form 300 can then be folded in half along the dotted line shown, separating the vertical region lengths 305, 306 in half or essentially half. The top edges of the horizontal regions can be flush. The outer edges having the binding material 309, 310 can then be folded over to make a seam, thus forming a barrier garment embodiment.

In some embodiments, the barrier is formed as one integrated unit through dip molding or dipping. Some embodiments of the barrier, as well as other garments, are manufactured using a mold form or mandrel or former or mold. The mold is made of any suitable material, including but not limited to ceramic, glass, metal and/or alloy, and/or hard plastic. The garments that can be made with a mold form embodiment include the barrier, latex or non-latex novelty underwear, and other garments.

In an embodiment, dip molding allows for a thin material to be used as the garment. Current fashion undergarments are not dip molded. In an embodiment, dip molding allows for a variety of different solutions to be used as the undergarment—which allows for flexibility of taste, smell, texture, and appearance values. This also allows for a change of underlying material due to discovered attributes of viruses, user's allergies, and/or materials regulations. In an embodiment, dip molding as described allows for a manufacturer to avoid having to glue, sew, or otherwise attach pieces of a garment together to form a wearable garment. In an embodiment, dip molding allows for an inexpensive and/or biodegradable version of the garment to be manufactured, thus supporting, e.g., the disposability of the garment.

Some embodiments of the mold form are shaped in a semi-anatomical manner. FIGS. 25A to 25B show embodiments of a semi-anatomical mold 250 that can be used to manufacture some embodiments of the barrier. This mold embodiment includes a general shape of a barrier. FIG. 25A shows a mold form that contains a genital-portion crease 253 and a back-portion crease 251 that can produce an embodiment of a barrier similar to that shown in FIGS. 1A to 1C, FIG. 2, FIG. 3, and FIGS. 4A to 4B. FIG. 25B shows a mold form that does not contain creases 251 or 253 and instead has a smooth genital portion 256 and a smooth torso and back portion 255; this mold embodiment can produce an embodiment of the barrier similar to that shown in FIGS. 5A to 5C, FIG. 6, FIG. 7, and FIGS. 8A to 8B. The bottom portion of the semi-anatomical mold embodiment can be flat 252, can be conical 257, or can be any other shape known in the art. When a barrier 10 is created using a semi-anatomical mold form 250 and is then flattened to cut leg openings, the conical shape 257 or another shape of the bottom can ease the cutting process while minimizing loss of material.

Figure 21A:
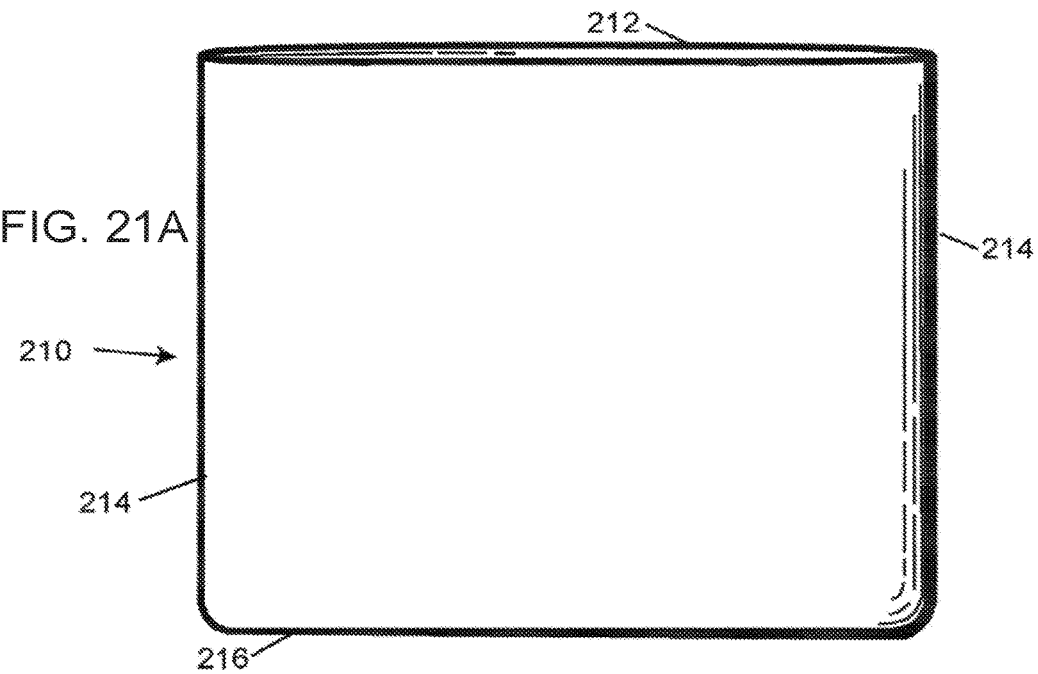
FIG. 21A shows a front view of a flat mold embodiment for manufacturing a garment embodiment of the present invention.
Figure 21B:
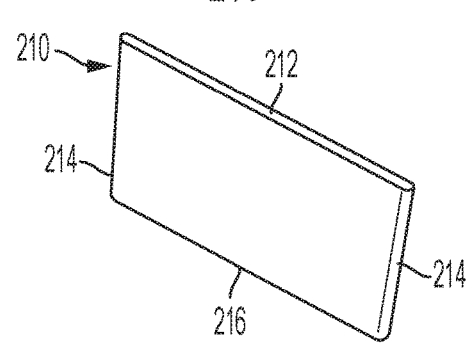
FIG. 21B shows a top view of a flat mold embodiment for manufacturing a garment embodiment of the present invention.
Figure 21D:
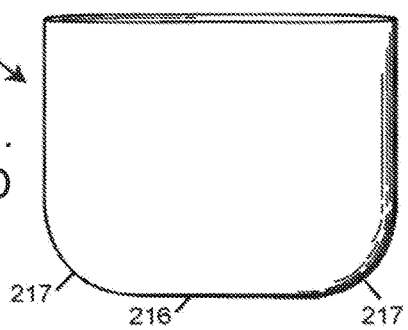
FIG. 21D shows a front view of a flat mold embodiment for manufacturing a garment embodiment of the present invention.
Figure 21C:
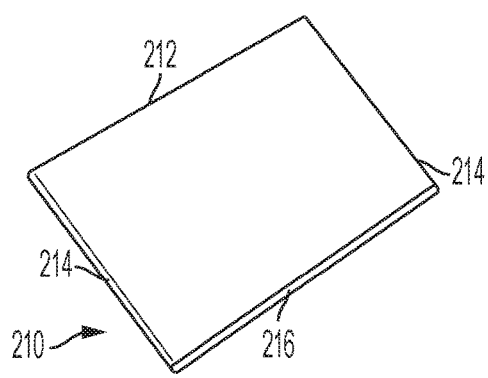
FIG. 21C shows a front view of a flat mold embodiment for manufacturing a garment embodiment of the present invention.
Figure 21E:
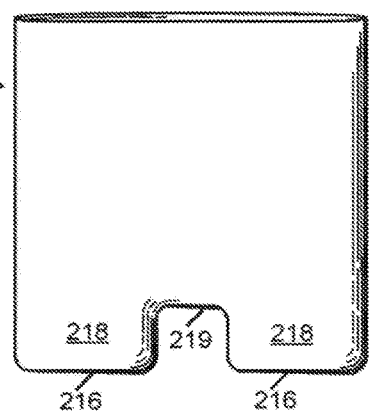
FIG. 21E shows a front view of a flat mold embodiment for manufacturing a garment embodiment of the present invention.
Figures 22A, 22B, 22C:
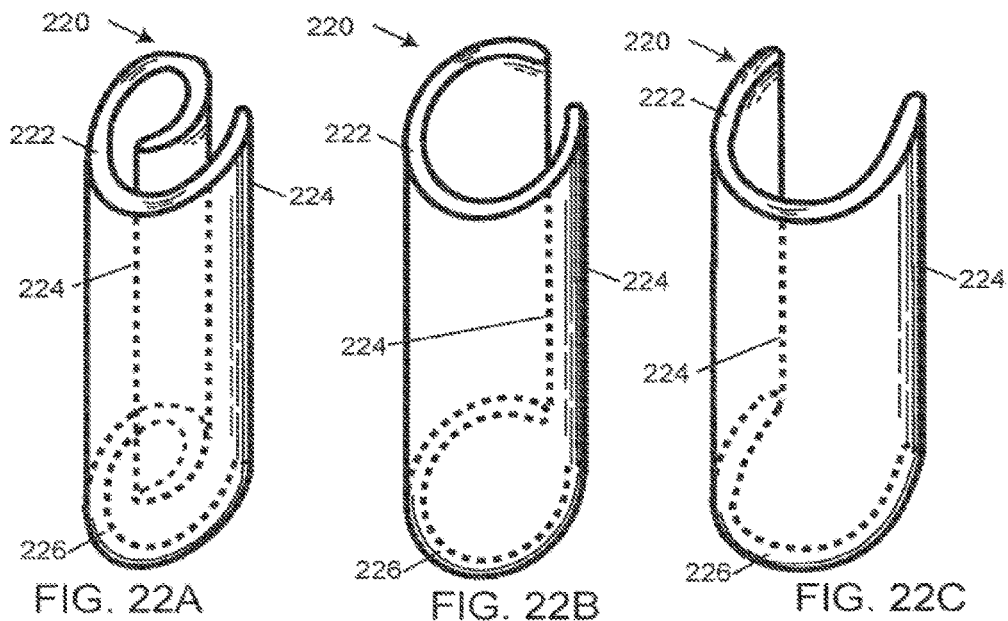
FIG. 22A shows a front and top view of a curved mold embodiment for manufacturing a garment embodiment of the present invention.
FIG. 22B shows a front and top view of a curved mold embodiment for manufacturing a garment embodiment of the present invention.
FIG. 22C shows a front and top view of a curved mold embodiment for manufacturing a garment embodiment of the present invention.
Figure 22D:
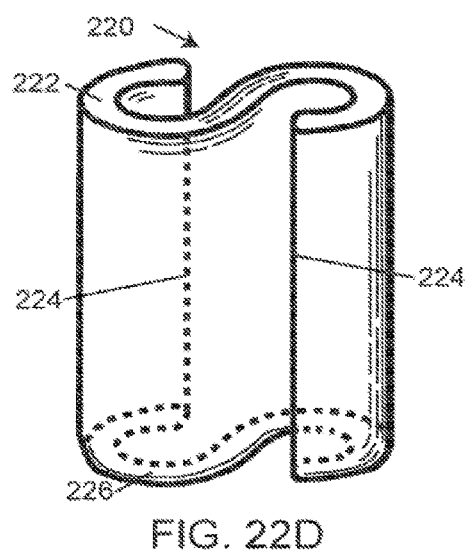
FIG. 22D shows a front and top view of a curved mold embodiment for manufacturing a garment embodiment of the present invention.

Other embodiments of the mold form are substantially planar and are not anatomically shaped. FIGS. 21A to 21E and FIGS. 22A to 22D show substantially planar mold embodiments. FIG. 21A shows a planar flat mold embodiment 210. FIG. 21B and FIG. 21C show additional views of the embodiment of the mold shown in FIG. 21A. FIGS. 22A to 22D show planar curved mold embodiments 220. Planar curved mold embodiments 220 create a similar shape of the material as do planar flat mold embodiments 210 once the material has been dried and removed from the mold, yet planar curved mold embodiments 220 take up less space in a production line and can allow for ease of dip molding, mass dip molding, and/or removal of the garment from the mold. Planar curved mold embodiments 220 can be curved in any manner to optimize their usability in an existing production line. The mold embodiments can produce an embodiment of the barrier similar to that shown in FIGS. 9A to 9E and FIGS. 10A to 10D, can produce other embodiments of the barrier, or can produce other garments.

In some embodiments, semi-anatomical mold embodiment 250, planar flat mold embodiment 210, and/or planar curved mold embodiment 220 have a top portion 258, 212, or 222 (respectively) manufactured with any of the various fasteners available in the art, such that the molds 250, 210, and 220 can be attached to dip-molding machinery. In some embodiments, the mold embodiment is hollow. In some embodiments, the mold embodiment is not hollow. In some embodiments of planar mold forms, sides 214, sides 224, bottom 216, and bottom 226, are curved to minimize the appearance of edges in the garment. In some embodiments, the mold used is a planar mold that is bent or curved into a shape to allow for ease of dip molding, mass dip molding, and/or removal of the garment from the mold. In some embodiments, such as in FIG. 21D, the mold is a planar mold in a U-shape with curved corners 217 to allow for less waste of material and/or solution. In some embodiments, such as in FIG. 21E, the planar mold has a cut-out 219 in the middle of the bottom part of the mold simulating the legs 218 of a boy-short version. Planar curved mold embodiments similar to those shown in FIGS. 22A to 22D can also contain curved corners 217 or cut-out 219.

Figure 20:
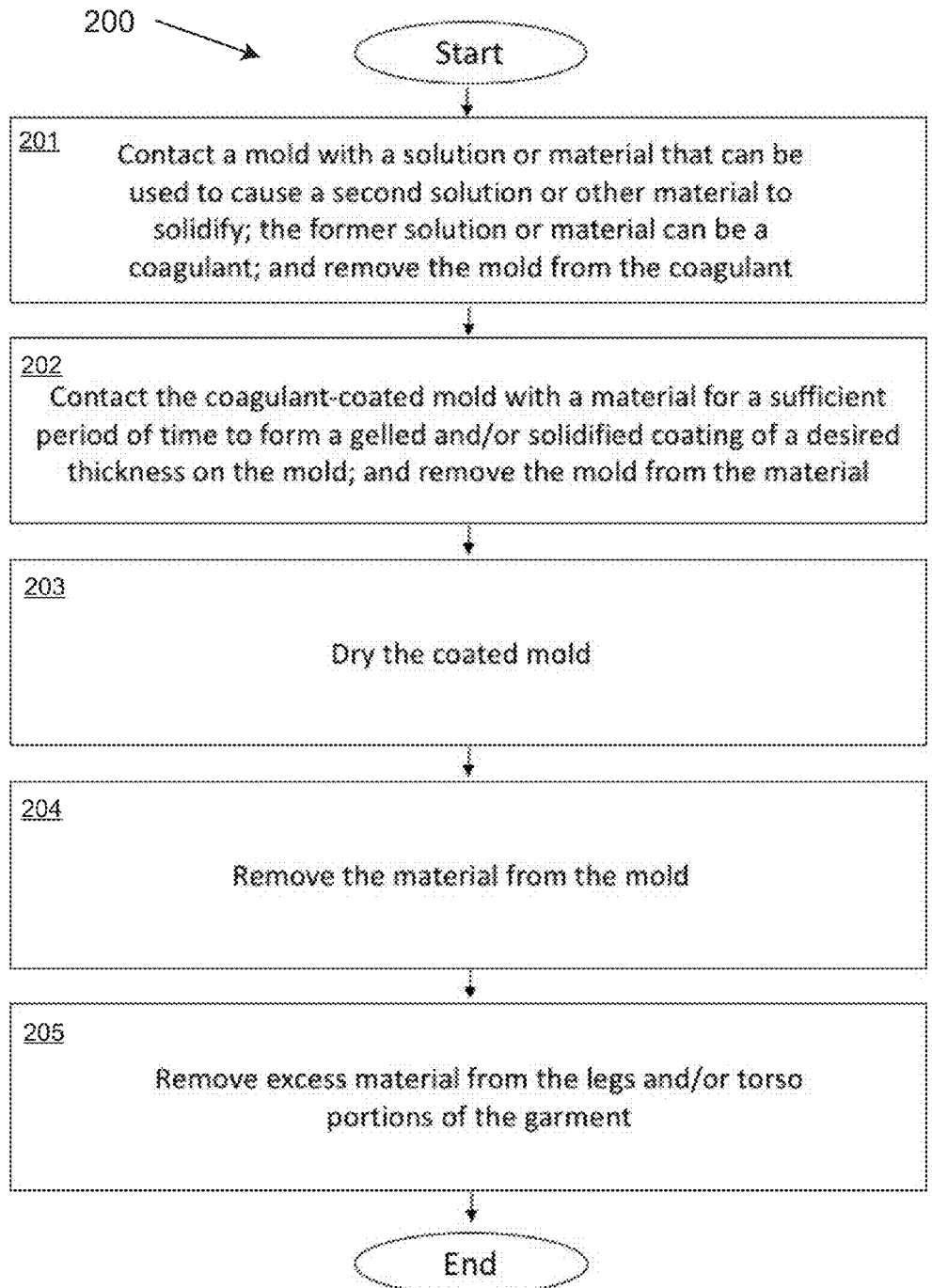
FIG. 20 shows a flow chart illustrating a manufacturing process embodiment for manufacturing a garment embodiment of the present invention.

Various embodiments of a manufacturing process to produce a barrier garment embodiment described herein can also be used to produce a latex, non-latex, or other material garment, underwear, etc. To manufacture an embodiment of barrier 10 or another garment, a process 200 illustrated in FIG. 20 is followed:

Step 1 (201): The mold is contacted with a solution or material that can be used to cause a second solution or other material to solidify; the former solution or material can be a coagulant. The mold is removed from the coagulant, such that a layer of coagulant of a desired thickness remains on the mold. The removal of the mold from the coagulant can be by machine, by hand, and/or by air. The desired thickness is dependent upon the necessary thickness of the coagulant needed for reacting with and/or acting in concert with the later solution or material(s) added, for example, one or more of the materials listed in Step 2 below. In some embodiments, Step 1 is repeated before Step 2 occurs. In some embodiments, the coagulant-coated mold is dried before Step 2 occurs.

Step 2 (202): The mold is contacted with a material such as natural rubber latex, synthetic latex, latex, butyl rubber, polyethylene, linear low density polyethylene (LLDPE), low density polyethylene (LDPE), high density polyethylene, polypropylene, olefin copolymer, styrene/butadiene rubber (SBR), polyurethane, polyisoprene, polyvinylidene chloride, polychloroprene, carboxylated acrylonitrile butadiene rubber, nitrile, graphene, spinifex grass, other grass, nano-cellulose, vegan material, hypoallergenic material, organic material, superelastomer, other elastomer, other polymer, other copolymer, other polyolefin, and/or a combination of any of these materials, for a sufficient period of time to form a gelled and/or solidified coating of a desired thickness on the mold. The material can also include additives such as ammonia, water, soap, softening agents, accelerators, antioxidants, salts, stabilizers, defoamers, dispersants, wetting agents, de-aeraters, antifungal and antibacterial compounds, preservatives, pigments, anticoagulants, lubricants, potassium laureate, potassium oleate, potassium hydroxide, sulfur, zinc oxide, corn starch, sulfur, chlorine, chalk, silica, clay, and other additives. The material-coated mold is removed from the excess material. The removal of the mold from the material can be by machine, by hand, and/or by air. In some embodiments, this step is repeated one or more times before Step 4 occurs; in some embodiments, a different material is used upon a different contact with the mold.

Step 3 (203): The coated mold is dried. In an embodiment, the drying can involve any of the various methods available in the art.

Step 4 (204): The material is removed from the mold. In an embodiment, the removal from the mold is described herein. In an embodiment, the removal from the mold can involve any of the various methods available in the art.

Step 5 (205): Excess material is removed from the legs and/or the torso portions of the barrier. In an embodiment, the removal can involve die-cutting. In an embodiment, the removal can involve any of the various methods available in the art. In an embodiment, both the front and back of the garment are cut in a similar fashion at the same time with a cutting press.

In some embodiments, the mold is never in contact with and/or removed from the coagulant. For example, the manufacturing process begins with Step 2 as listed above.

In some embodiments, the mold is shifted and/or rotated while being contacted with material and/or coagulant to spread the material and/or coagulant along a portion of and/or the entire surface of the mold.

In some embodiments, the temperature of the mold is varied to extend or to limit the amount of time the mold is contacted with material and/or to change the properties of the material and/or the texture of the barrier.

In some embodiments, the mold is coated with material more than one time. In some embodiments, the mold is coated with more than one type of material.

In some embodiments, the thickness of the barrier can be varied by changing the ingredients in the coagulant and/or the material, and/or by dipping certain portions of the barrier more than once.

In some embodiments, the mold is contacted with coagulant by dipping said mold into said coagulant. In some embodiments, the mold is contacted with material by dipping said mold into said material. In some embodiments, the mold is contacted with coagulant by pouring said coagulant into said mold, and then excess coagulant is removed from said mold. In some embodiments, the mold is contacted with material by pouring said material into said mold, and then excess material is removed from said mold.

In some embodiments, between Step 3 and the end of the process described above, one or more of the following steps occurs, in any order: (a) the material-coated mold is leached to remove impurities; (b) the material is cured in an oven to set the material; (c) the material is vulcanized; (d) the edges of the material are thickened, by adding additional material, rolling the existing material, or by another means; and/or (e) powder is applied to said material.

In some embodiments, Step 4 is facilitated by applying powder to the material prior to removing it from the mold.

In some embodiments, the material is removed from the mold by hand. In other embodiments, the material is removed from the mold by a stream of air.

Figure 26:
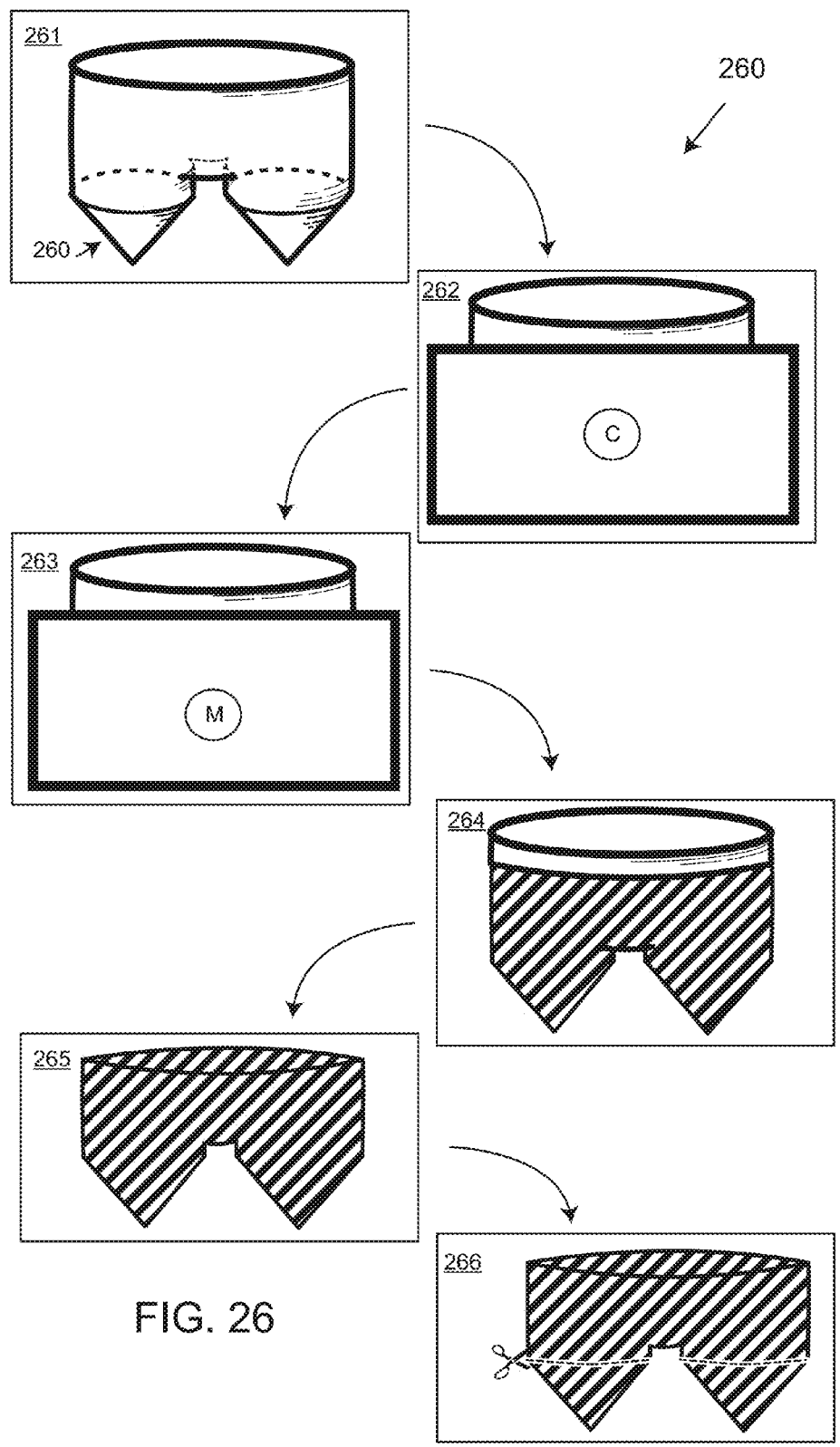
FIG. 26 shows a flowchart of a manufacturing process embodiment using a semi-anatomical mold form embodiment of the present invention.

FIG. 26 shows an embodiment of a manufacturing process 260 that can be used to manufacture a barrier 10 or another garment. A mold form embodiment 260 (shown in 261) is dipped into and removed from coagulant (C) (shown in 262) and then dipped into and removed from material (M) (shown in 263). 264 shows mold form embodiment 260 after it has been removed from material and is coated with material. 265 shows the material after it has dried and has been removed from said mold form embodiment. 266 shows where the leg holes will be cut.

FIG. 23 and FIG. 24 show embodiments of manufacturing processes 230 and 240, respectively, that can be used to manufacture a barrier 10 or another garment. A planar flat mold form embodiment 210 or a planar curved mold form embodiment 220 (shown in 231 and 241) is dipped into and removed from coagulant (C) (shown in 232 and 242) and then dipped into and removed from material (M) (shown in 233 and 243). 234 shows planar flat mold form embodiment 210 after it has been removed from material and is coated with material. 244 shows planar curved mold form embodiment 220 after it has been removed from material and is coated with material. 235 shows the material after it has dried and has been removed from planar flat mold form embodiment 210, and 235 shows the material after it has dried and has been removed from planar curved mold form embodiment 220. 236 shows where the leg holes will be cut on planar flat mold form embodiment 210, and 246 shows where the leg holes will be cut on planar curved mold form embodiment 220.

In some embodiments, the barrier is manufactured so as to include an extra piece of material not removed from the thigh region. This extra piece of material still attached to the thigh region is used to cover the barrier when folded into a compact item. In some embodiment, the extra piece or extension of material extends from a portion of the top of the torso, and folds down since there is no opposing piece of material to serve as tension or friction inducing in order to keep the extended material from folding down. In some embodiments, a separate carrying case is provided to hold the garment. The case may be made of similar material, or a different material, than the garment.

The modifications listed herein and other modifications can be made by those in the art without departing from the ambit of the invention. Although the invention has been described above with reference to specific embodiments, the invention is not limited to the above embodiments and the specific configurations shown in the drawings. For example, some components shown can be combined with each other as one embodiment, and/or a component can be divided into several subcomponents, and/or any other known or available component can be added. The operation processes are also not limited to those shown in the examples. Those skilled in the art will appreciate that the invention can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

What is claimed is:

1. A mold, comprising:
   a housing having a front portion, a back portion, a right and a left side portions, and a bottom portion, so that the front, back, right side, left side, and bottom portions are connected to form the housing as a three-dimensional structure, wherein the housing allows for being dip-molded in a solution which at least semi-solidifies on the housing, wherein the front and back portions are planar curved.

2. The mold of claim 1, wherein the housing is at least one of: filled with solid material, hollow, and partially filled with material.

3. The mold of claim 1, wherein the housing allows for the use of an apparatus to attach to a top portion of the housing, the apparatus being used to do at least one of: holding the housing during dip-molding, holding the housing during drying, and holding the housing during removal of material.

4. The mold of claim 3, wherein the apparatus is at least one of: a gripping device, a wire, a hanging device, a screwed-in device, and a magnetic device.

5. The mold of claim 1, wherein the housing is made of at least two materials wherein a first of the at least two materials is a material resistant to corrosion, and a second of the at least two materials is a material which does not permanently bind with polymer solution, wherein the second of the at least two materials is layered over the first of the at least two materials.

6. The mold of claim 1, wherein the housing is composed of a material that is coatable with a completely non-permeable material, a partially non-permeable material, a partially pliable material, and a completely pliable material.

7. The mold of claim 1, wherein the housing is coatable by a coating that is an elastomeric material having a thickness of one of: 0.33 millimeters, less than 0.33 millimeters, and greater than 0.33 millimeters.

8. The mold of claim 1, wherein the housing has a material coating which allows for at least one of: a formation of a membrane from a solidifying solution, a removal of a membrane formed from a solidifying solution on the housing, and resistance to sharp cutting instruments.

9. A mold on which a garment can be formed, comprising:
   a rectangular-shaped housing having a front portion, a back portion, a left side portion, and a right side portion, wherein the front portion, back portion, and left side and right side portions, are connected to each other to form a three-dimensional rectangular-shaped housing;
   a first cylindrical housing, wherein a top portion edge of the first cylindrical housing is connected to a bottom portion edge of the rectangular-shaped housing, so that the top portion edge of the first cylindrical housing is connected with the left side portion, the front portion, and the back portion;

a second cylindrical housing, wherein a top portion edge of the second cylindrical housing is connected to the bottom portion edge of the rectangular-shaped housing, so that the top portion edge of the first cylindrical housing is connected with the right side portion, the front portion, and the back portion; and, a middle portion having a front edge, a back edge, a right side edge and a left side edge, wherein the middle portion front edge is connected to the rectangular-shaped housing front edge, the middle portion back edge is connected to the rectangular-shaped housing back edge, the middle portion right side edge is connected to the second cylindrical housing, and the middle portion left side edge is connected to the first rectangular-shaped housing.

10. The mold of claim 9, wherein the first cylindrical housing and the second cylindrical housing are each at least one of: an ellipsoid and an ovoid.

11. The mold of claim 9, further comprising: a first conical portion connected to a bottom portion edge of the first cylindrical housing; and a second conical portion connected to a bottom portion edge of the second cylindrical housing.

12. The mold of claim 9, wherein the housing is made of at least two materials wherein a second of the at least two materials is a material which does not bind with coagulants, wherein the second of the at least two materials is layered over a first of the at least two materials.

13. The mold of claim 9, wherein the housing is coatable with a completely non-permeable material, a partially non-permeable material, a partially pliable material, and a completely pliable material.

14. The mold of claim 9, wherein the housing has a material coating which allows for at least one of: a formation of a membrane from a solidifying solution, a removal of a membrane formed from a solidifying solution on the housing, and resistance to sharp cutting instruments.

15. The mold of claim 9, wherein the housing is at least one of: filled with solid material, hollow, and partially filled with material.

16. The mold of claim 9, wherein the housing allows for the use of an apparatus to attach to a top portion of the housing, the apparatus being used to do at least one of: holding the housing during dip-molding, holding the housing during drying, and holding the housing during removal of material.

17. The mold of claim 16, wherein the apparatus is at least one of: a gripping device, a wire, a hanging device, a screwed-in device, and a magnetic device.

18. The mold of claim 9, wherein the first and second cylindrical shaped housings are sized to fit a thigh of a human.

19. The mold of claim 1, wherein the housing is made of at least two materials wherein a second of the at least two materials is a material which does not bind with coagulants, wherein the second of the at least two materials is layered over a first of the at least two materials.

20. The mold of claim 9, wherein the housing is made of at least two materials wherein a first of the at least two materials is a material resistant to corrosion, and a second of the at least two materials is a material which does not permanently bind with polymer solution, wherein the second of the at least two materials is layered over the first of the at least two materials.

* * * * *